(12) United States Patent
Nikonov et al.

(10) Patent No.: US 11,186,585 B2
(45) Date of Patent: Nov. 30, 2021

(54) COMPOSITIONS AND METHODS OF ENHANCING OPIOID RECEPTOR ENGAGEMENT BY OPIOID HEXADIENOATES AND OPTIONALLY SUBSTITUTED HEXADIENOATES

(71) Applicant: Kappa-Pharma LLC, Alachua, FL (US)

(72) Inventors: Georgiy Nikonov, Gainsville, FL (US); Levon Isakulyan, New York, NY (US); Michael Voronkov, Pennington, NJ (US)

(73) Assignee: Kappa-Pharma LLC, Alachua, FL (US)

( * ) Notice: Subject to any disclaimer, the term of this patent is extended or adjusted under 35 U.S.C. 154(b) by 0 days.

(21) Appl. No.: 16/540,058

(22) Filed: Aug. 14, 2019

(65) Prior Publication Data

US 2020/0055864 A1 Feb. 20, 2020

Related U.S. Application Data

(60) Provisional application No. 62/885,311, filed on Aug. 11, 2019, provisional application No. 62/719,417, filed on Aug. 17, 2018.

(51) Int. Cl.
| | |
|---|---|
| *C07D 489/02* | (2006.01) |
| *C07C 229/38* | (2006.01) |
| *A61P 25/36* | (2006.01) |
| *C07D 221/28* | (2006.01) |
| *A61K 9/00* | (2006.01) |

(52) U.S. Cl.
CPC ............ *C07D 489/02* (2013.01); *A61P 25/36* (2018.01); *C07C 229/38* (2013.01); *C07D 221/28* (2013.01); *A61K 9/0053* (2013.01)

(58) Field of Classification Search
CPC .................................................. C07D 489/02
See application file for complete search history.

(56) References Cited

U.S. PATENT DOCUMENTS

| | | | |
|---|---|---|---|
| 5,750,534 A | 5/1998 | Yoa-Pu | |
| 6,569,449 B1 * | 5/2003 | Stinchcomb | A61K 9/7084 424/443 |
| 6,703,398 B2 | 3/2004 | Hu | |
| 2005/0137141 A1 | 6/2005 | Hilfinger | |
| 2011/0190267 A1 | 8/2011 | Franklin | |
| 2011/0245288 A1 | 10/2011 | Stinchcomb | |
| 2014/0112951 A1 | 4/2014 | Tang | |
| 2017/0152266 A1 * | 6/2017 | Thottathil | C07D 489/08 |
| 2017/0196851 A1 * | 7/2017 | Thottathil | C07D 489/12 |
| 2018/0236082 A1 | 8/2018 | Miwa | |
| 2020/0055864 A1 | 2/2020 | Nikonov | |

FOREIGN PATENT DOCUMENTS

| | | |
|---|---|---|
| CN | 1107333 A | 8/1995 |
| CN | 1204649 A | 1/1999 |
| CN | 104968338 B | 9/2018 |
| EP | 129947 A2 * | 2/1985 |
| EP | 0170090 B1 | 9/1989 |
| EP | 0615756 A1 | 9/1994 |
| EP | 1149836 A1 | 10/2001 |
| EP | 2910242 | 4/2019 |
| RU | 2215741 C1 | 11/2003 |
| RU | 2221566 C1 | 1/2004 |
| TW | I226239 B1 | 1/2005 |
| TW | I448287 B1 | 8/2014 |
| WO | 2002/09768 A2 | 2/2002 |
| WO | 2003/070191 A2 | 8/2003 |
| WO | 2005/009377 A2 | 2/2005 |
| WO | 2007/022535 A2 | 2/2007 |
| WO | 2009/092071 A2 | 7/2009 |
| WO | 2010/112942 A1 | 10/2010 |
| WO | 2011/007247 A1 | 1/2011 |
| WO | 2011/083304 A1 | 7/2011 |

(Continued)

OTHER PUBLICATIONS

Mark Connor and MacDonald J Christie "Opioid Receptor Signaling Mechanisms" Clinical and Experimental Pharmacology and Physiology 1999 26, 493-499.*
Al-Hasani, "Molecular Mechanisms of Opioid Receptor-dependent Signaling and Behavior" Anesthesiology 2011; 115:1363-81.*
Quock et. al., "The -Opioid Receptor: Molecular Pharmacology, Signal Transduction, and the Determination of Drug Efficacy" Pharmacological Reviews 1999, 51(3), 503-532.*
"Sorbic Acid" Van Nostrand's Scientific Encyclopedia, 2006 John Wiley & Sons, Inc. 1-12.*
Kupchan "Baccharin, a Novel Potent Antileukemic Trichothecene Triepoxide from Baccharis megapotamica" Journal of the American Chemical Society 1976, 98:22, 7092-7093.*

(Continued)

*Primary Examiner* — David K O'Dell
(74) *Attorney, Agent, or Firm* — Peter Tu

(57) ABSTRACT

The present invention relates to opiate derived compositions and their antagonists useful in therapeutic areas associated with opioid receptor modulation. A 3-hexadienoate modification of the opioids is formulated to improve opiates' engagement of the opioid receptors when given orally. A 3-hexadienoate modification of Nalbuphine or a pharmaceutically acceptable salt of thereof to improve quality of pain management when given intravenously, intranasally, transdermally, sublingually, rectally, topically, intramuscularly, subcutaneously or via inhalation. A 3-hexadienoate modification of the opioids antagonists is formulated to improve inhibition of the opioid receptors when given orally. A 3-hexadienoate modification of Naloxone or a pharmaceutically acceptable salt of thereof to improve quality of Sobering when given intravenously, intranasally, transdermally, sublingually, rectally, topically, intramuscularly, subcutaneously or via inhalation.

4 Claims, 14 Drawing Sheets

(5 of 14 Drawing Sheet(s) Filed in Color)

(56) References Cited

FOREIGN PATENT DOCUMENTS

| WO | 2013/093931 A2 | 6/2013 | | |
|---|---|---|---|---|
| WO | 2014/059558 A1 | 4/2014 | | |
| WO | WO-2018191472 A1 | * | 10/2018 | ............... C07K 5/08 |

OTHER PUBLICATIONS

Sinuco Free and Glycosidically Bound Volatile Components From Pineapple (*Ananas comosus* L.) Var. Perolera Revista Colombiana De Química, vol. 33, No. 1 DE 2004.*

Duarte "Opium and Opioids: A Brief History" Rev Bras Anestesiol 2005; 55: 1: 135-146.*

Lufty "Buprenorphine: A Unique Drug with Complex Pharmacology" Curr Neuropharmacol. Oct. 2004; 2(4): 395-402.*

Kuzmina "Geometric parameters as a criterion for assessment of the bioactive conformations of opiate receptor ligands." Russian Chemical Bulletin, International Edition, vol. 55, No. 9, pp. 1516-1522, Sep. 2006.*

Bruce J. Aungst et al., Prodrugs for Improved Oral Nalbuphine Bioavailability: Inter-Species Differences in the Disposition of Nalbuphine and Its Acetylsalicylate and Anthranilate Esters, International Journal of Pharmaceutics, 1987, pp. 199-209, vol. 38, issue 1-3, Elsevier, USA.

Adam Bisaga, What Should Clinicians Do as Fentanyl Replaces Heroin?, Addiction, 2019, pp. 781-786, vol. 114, John Wiley & Sons, Hoboken, New Jersey.

Roger Chou et al., Management of Suspected Opioid Overdose With Naloxone by Emergency Medical Services Personnel, Comparative Effectiveness Review, 2017, No. 193, Agency for Healthcare Research and Quality, Washington, D.C.

Iman A. Elkiweri et al., Competitive Substrates for P-Glycoprotein and Organic Anion Protein Transporters Differentially Reduce Blood Organ Transport of Fentanyl and Loperamide: Pharmacokinetics and Pharmacodynamics in Sprague-Dawley Rats, Anesth. Analg., 2009, pp. 149-159, vol. 108(1), NIH, United States.

Jia-You Fang, Transdermal Delivery of Nalbuphine and Nalbuphine Pivalate from Hydrogels by Passive Diffusion and Iontophoresis, Arzneimittel-Forschung (Drug Research), 2001, pp. 408-413, vol. 51, issue 5, Elsevier B.V., Amsterdam.

Rough-Yee Han, Mucoadhesive Buccal Disks for Novel Nalbuphine Prodrug Controlled Delivery: Effect of Formulation Variables on Drug Release and Mucoadhesive Performance, International Journal of Pharmaceutics, 1999, pp. 201-209, vol. 177, issue 2, Elsevier, Amsterdam.

Jeng-Fen Huang et al., The Effects of Electrically Assisted Methods on Transderam Delivery of Nalbuphine Benzoate and Sebacoyl Dinalbuphine Ester from Solutions and Hydrogels, International Journal of Pharmaceutics, 2005, pp. 162-171, vol. 297, Elsevier, Amsterdam.

Baohua Huang et al., Human Plasma-Mediated Hypoxic Activation of Indolequinone-Based Naloxone Pro-Drugs, Bioorganic & Medicinal Chemistry Letters, 2009, pp. 5016-5020, vol. 19(17), Elsevier, Amsterdam.

Munir A. Hussain et al., Improved Buccal Delivery of Opioid Analgesics and Antagonists with Bitterless Prodrugs, Pharmaceutical Research, 1988, pp. 615-618, vol. 5(9), Plenum Publishing Corp., New York.

S. Lazar et al., Synthesis and Biological Activity of the Phosphate and Sulfate Esters of Naloxone and Naltrexone, European Journal of Medicinal Chemistry, 1994, pp. 45-53, vol. 29(1), Elsevier, Paris.

Fang-I. Liu et al., Biodegradable Polymeric Microspheres for Nalbupine Prodrug Controlled Deliver: In Vitro Characterization and In Vivo Pharmacokinetic Studies, International Journal of Pharmaceutics, 2003, pp. 23-31, vol. 257, Elsevier, Amsterdam.

Rachael Rzasa Lynn et al., Naloxone Dosage for Opioid Reversal: Current Evidence and Clinical Implications, Therapeutic Advances in Drug Society Review, 2018, pp. 63-88, vol. 9(1), Sage Journals, United Kingdom.

Rebecca Mcdonald et al., Pharmacokinetics of Concentrated Naloxone Nasal Spray for Opioid Overdose Reversal: Phase I Healthy Volunteer Study, Addiction, 2017, pp. 484-493, vol. 113, John Wiley & Sons, Hoboken, New Jersey.

Li-Heng Pao et al., High-Performance Liquid Chromatographic Method for the Simultaneous Determination of Nalbuphine and Its Prodrug, Sebacoyl Dinalbuphine Ester, in Dog Plasma and Application to Pharmacokinetic Studies in Dogs, Journal of Chromatography B: Biomedical Sciences and Applications, 2000, pp. 241-247, vol. 746, issue 2, Elsevier, Amsterdam.

Xuemei Peng et al., Pharmacological Properties of Bivalent Ligands Containing Butorphan Linked to Nalbuphine and Nalaxone at μ, δ and κ Opioid Receptors, Journal of Medicinal Chemistry, 2007, pp. 2254-2258, vol. 50(9), American Chemical Society, United States.

K.C. Sung et al., Controlled Release of Nalbuphine Prodrugs from Biodegradable Polymeric Matrices Influence of Prodrug Hydrophilicity and Polymer Composition, International Journal of Pharmaceutics, 1998, pp. 17-25, vol. 172, Elsevier, Amsterdam.

K.C. Sung et al., Transdermal Delivery of Nalbuphine and Its Prodrugs, by Electroporation, European Journal of Pharmaceutical Sciences, 2003, pp. 63-70, vol. 18, Elsevier, Amsterdam.

I.V. Ukrainets et al., Studies of 3-O-Acyl Derivatives of Naloxone as Its Potential Prodrugs, Chemistry of Heterocyclic Compounds, 2009, pp. 405-416, vol. 45(4), Springer Science+Business Media, Inc., Germany.

Jhi-Joung Wang et al., Submicron Lipid Emulsion as a Drug Delivery System for Nalbuphine and Its Prodrugs, Journal of Controlled Release, 2006, pp. 140-149, vol. 115, Elsevier, Amsterdam.

Can-Jing Wei et al., Synthesis and Antitumor Activities of Sinomenine Derivatives on Rings A and C, Journal of Asian Natural Products Research, 2017, pp. 277-291, vol. 20, Taylor & Francis Group, United Kingdom.

* cited by examiner

COMPOSITIONS AND METHODS OF ENHANCING OPIOID RECEPTOR ENGAGEMENT BY OPIOID HEXADIENOATES AND OPTIONALLY SUBSTITUTED HEXADIENOATES

This application is a Non-Provisional of prior U.S. Provisional Patent Ser. No. 62/719,417, entitled "OPIATE DERIVED COMPOSITIONS AND METHODS" and prior U.S. Provisional Patent Application Ser. No. 62/885,311, entitled "COMPOSITIONS AND METHODS OF ENHANCING OPIOID RECEPTOR ENGAGEMENT BY OPIOID HEXADIENOATES AND OPTIONALLY SUBSTITUTED HEXADIENOATES", to each of which priority under 35 U.S.C. § 119 is claimed.

FIELD OF THE INVENTION

The present invention relates to opiate derived compositions, used in therapeutic areas associated with opioid receptor modulation.

BACKGROUND

Nalbuphine (Nubain) was launched in 1979 as an analgesic for moderate to severe pain and has effectively been used in the clinic since. It is primarily used in conjunction with anesthetics for pre- and post-operative analgesia and in labor and delivery for acute and chronic pain management. Recently its uses have been expanded to the treatment of locomotive disorders, dermatological conditions such as pruritus and addiction management.

It has also been recently shown that Nalbuphine could prevent opiate tolerance and dependence in chronic pain management. It is the only narcotic analgesic of its type that is not subject to the Controlled Substances Act, an indication of its safe utility. Nalbuphine has a low oral bioavailability.

There are known Nalbuphine prodrugs designed to improve its pharmacokinetic and pharmacodynamic properties. Merriam-Webster defines a prodrug as a pharmacologically inactive substance that is the modified form of a pharmacologically active drug to which it is converted (as by enzymatic action) in the body. Thus, Franklin (WO 2010-GB52211) teaches that Nalbuphine could be modified at phenolic hydroxyl residue.

Furthermore, Nalbuphine could be coupled to an amino acid or short peptide (WO 2011007247, A1). Also, Nalbuphine could be modified with dicarboxylic acid linked amino acid and peptide (WO 2010112942, A1). Further yet, Nalbuphine could be modified with carbomate moiety linked amino acid and peptide (WO 2009092071, A2). Moreover, Jenkins (WO 2007022535, A2) teaches that Nalbuphine could be further modified on its phenolic or nitrogen moiety.

Wang teaches that Nalbuphine could be converted to ester prodrug (Journal of Controlled Release, Volume: 115, Issue: 2, Pages: 140-149, Journal, 2006,). Hu (Jan. 11, 2005, TW 226239, B) teaches that delivery systems and Nalbuphine prodrugs which increase its bioavailability. More specifically, formulation to increase Nalbuphine's bioavailability includes vegetable oils, a co-solvent, and an effective amount of a Nalbuphine ester prodrug or a pharmaceutically acceptable salt thereof. One objective of prodrugs is to increase the oral bioavailability of Nalbuphine and prolong the retention time of Nalbuphine in a body, thereby maintaining a longer analgesic period of time, as well as reducing the analgesic cost.

Hilfinger (US 20050137141, A1) teaches of Nalbuphine including a pharmaceutical species and an amino acid having a covalent bond to the pharmaceutical species. Huang (International Journal of Pharmaceutics, Volume: 297, Issue: 1-2, Pages: 162-171, Journal, 2005) teaches of the effects of iontophoresis and electroporation on transdermal delivery of Nalbuphine (NA) and its two novel prodrugs: Nalbuphine benzoate (NAB) and sebacoyl dinalbuphine ester (SDN) from solutions as well as from hydrogels.

Crooks (WO 2005009377, A2) teaches that forming duplex prodrugs including Nalbuphine can provide significant increase in the transdermal flux of drugs across human skin. Uhrich (WO 2002009768, A2) teaches of therapeutic polyesters and polyamides of Nalbuphine. Hu (EP 1149836, A1) teaches of preparation of polynalbuphine derivatives. Pao (Journal of Chromatography, B: Biomedical Sciences and Applications, Volume: 746, Issue: 2, Pages: 241-247, Journal, 2000) teaches of bioavailability of sebacoyl dinalbuphine ester.

Han (International Journal of Pharmaceutics, Volume: 177, Issue: 2, Pages: 201-209, Journal, 1999) teaches of Mucoadhesive buccal disks for novel Nalbuphine prodrug controlled delivery: effect of formulation variables on drug release and mucoadhesive performance. Sung (International Journal of Pharmaceutics, Volume: 172, Issue: 1-2, Pages: 17-25, Journal, 1998) teaches of controlled release of nalbuphine prodrugs from biodegradable polymeric matrixes: influence of prodrug hydrophilicity and polymer composition. Yoa-Pu (U.S. Pat. No. 5,750,534, A) teaches of Nalbuphine esters having long-acting analgesic action.

Shami (EP 85108258.6) teaches that Nalbuphine can be further modified into 3-acetylsalicylate. Additional Nalbuphine prodrugs are disclosed in U.S. Pat. No. 6,569,449, B1; CN 1107333, A; EP 615756, A1; and International Journal of Pharmaceutics, Volume: 38, Issue: 1-3, Pages: 199-209, Journal, 1987.

Pharmacokinetic and pharmacodynamic properties of Nalbuphine, its pharmaceutically acceptable salt, or ester, or its prodrug could be further modulated by various delivery systems. Thus Liu (International Journal of Pharmaceutics, Volume: 257, Issue: 1-2, Pages: 23-31, Journal, 2003) teaches that biodegradable polymeric microspheres for Nalbuphine prodrug controlled delivery. Sung (European Journal of Pharmaceutical Sciences, Volume: 18, Issue: 1, Pages: 63-70, Journal, 2003) teaches of transdermal delivery of nalbuphine and its prodrugs by electroporation. Fang (Arzneimittel-Forschung, Volume: 51, Issue: 5, Pages: 408-413, Journal, 2001) teaches of Transdermal delivery of nalbuphine and nalbuphine pivalate from hydrogels by passive diffusion and iontophoresis.

A distinction must be made between an improvement of oral bioavailability and an increase in opioid receptor engagement for these opioid derivatives. For example, esterification of phenoxy moiety of Nalbuphine (e.g. 3-docosanoate derivative of Nalbuphine) (NB-39) has been previously claimed to have improved oral bioavailability. However, when given orally, the cumulative analgesia produced by NB-39 was inferior to the equivalent dose of Nalbuphine in rats and humans. Furthermore, NB-39 did not significantly affect pupil dilation (miosis) in humans after oral administration that is indicative of inferior opioid receptor engagement.

Naloxone, sold under the brandname Narcan (and others), is a medication used to block the effects of opioids, especially in overdose situations. Naloxone may also be combined with an opioid (in the same pill or compound), to decrease the risk of opioid misuse. For instance, it could be added to the coating for a sustained release opiate compound, to prevent crushing of the sustained release compound, which could lead to an overdose.

When given intravenously, Naloxone typically works within two minutes, and when injected into a muscle, it works within five minutes. It may also be used as a nasal spray. The effects of Naloxone typically last for about half an hour to an hour. Thus, multiple doses and administration of Naloxone may be required, as the duration of action of most opioids is greater than that of Naloxone.

Administration of Naloxone to opioid-dependent individuals may cause symptoms of opioid withdrawal, such as, for example, restlessness, agitation, nausea, vomiting, increased heart rate and perspiration. To prevent this, small doses of Naloxone can be given every few minutes until the desired effect is reached.

In the individuals with prior history of heart disease or persons who take medications that negatively affect the heart, further heart problems have occurred. Naloxone appears to be safe in pregnancy, after having been given to and tested on a limited number of subjects.

Naloxone is a non-selective and competitive opioid receptor antagonist. It works by reversing the depression of the central nervous system and respiratory system caused by opioids. Naloxone was originally patented in 1961 and approved for opioid overdose treatment in the United States in 1971.

Naloxone, also known as N-allylnoroxymorphone or as 17-allyl-4,5α-epoxy-3,14-dihydroxymorphinan-6-one, is a synthetic morphinan derivative and was derived from oxymorphone (14-hydroxydihydromorphinone), an opioid analgesic—Oxymorphone, in turn, was derived from morphine, an opioid analgesic and naturally occurring constituent of the opium poppy.

Naloxone is a racemic mixture of two enantiomers, (−)-naloxone (levonaloxone) and (+)-naloxone (dextronaloxone), only the former of which is active at opioid receptors. The drug is a highly lipophilic, allowing it to rapidly penetrate the brain and to achieve a far greater brain to serum ratio than that of morphine. Opioid antagonists related to Naloxone include cyprodime, nalmefene, nalodeine, naloxol, and naltrexone.

The chemical half-life of Naloxone is such that injection and nasal forms have been marketed with 24-month and 18-month shelf-lives, respectively. A 2018 study noted that the nasal and injection forms presented as chemically stable to 36- and 28-months, respectively, which prompted an as yet incomplete five-year stability study to be initiated. This suggests that expired caches of material in community and healthcare settings may still be efficacious substantially beyond their labeled expiration dates.

Certain articles about opioid antagonists emphasize the shortcomings and problems with currently known formulations, and the need for an improved and more stable compound that may be used safely on patients suffering from opioid addiction.

An article by Adam Bisaga, entitled "What Should Clinicians Do As Fentanyl Replaces Heroin?" (published in Addiction, Vol. 114, pp. 781-86, at https://onlinelibrary.wiley.com/doi/epdf/10.1111/add.14522) describes that a high affinity antagonists may not suffice to block effects of fentanyl and their higher doses that border concerns over systematic safety may be required. Furthermore, fentanyl overdose prevention requires higher doses of naloxone and repeated dosing that is encumbered by much shorter overdose prevention window for fentanyl than heroin.

Roger Chou et al. describes in the article entitled "Management of Suspected Opioid Overdose With Naloxone by Emergency Medical Services Personnel" (published at In Comparative Effectiveness Review No. 193, at https://effectivehealthcare.ahrq.gov/sites/default/files/pdf/cer-193-naloxone-final_1.pdf) that existing dosing guidelines of naloxone may not be sufficient to prevent overdose by fentanyl and fentanyl analogues.

Rachael Rzasa Lynn et al. describes in the article entitled "Nalaxone Dosage for Opioid Reversal: Current Evidence and Clinical Implications" (published in Therapeutic Advances in Drug Society Review, Vol. 9(1), pp. 63-88, 2018 at https://www.ncbi.nlm.nih.gov/pmc/articles/PMC5753997/pdf/10.1177_2042098617744161.pdf) that double dose of naloxone administered to patient anesthetized with fentanyl produced no improvement in oxygen intake, while quadruple dose of naloxone produced significant improvements. Further he teaches that the interactions between the opioid agonist and the mu-opioid receptor may be the greatest determinant of the speed of recovery from the respiratory effects of many opioids, which may not markedly accelerate with increasing doses of naloxone, but rather respond to a minimum effective dose, while for compounds like buprenorphine, higher doses of naloxone may even lose efficacy. Then he cites numerous reports describe fentanyl overdoses initially unresponsive to IN naloxone and only transiently reversed with IV naloxone (if at all), requiring additional IV doses or continuous infusions to prevent recurrence of toxicity and respiratory depression.

IA. Elkiweri et al. describes in the article entitled "Competitive substrates for P-glycoprotein and organic anion protein transporters differentially reduce blood organ transport of fentanyl and loperamide: pharmacokinetics and pharmacodynamics in Sprague-Dawley rats" (published online in 2009 at https://www.ncbi.nlm.nih.gov/pubmed/19095843) that naloxone and fentanyl share a transporter for cellular influx that becomes saturated by a high plasma concentration of fentanyl, preventing rapid influx of naloxone across the BBB regardless of dose.

Rebecca McDonald et al. describes in the article entitled "Pharmacokinetics of concentrated naloxone nasal spray for opiod overdose reversal: Phase I healthy volunteer study" (published in Addiction, 113, pp. 484-93 at) that high concentration 2 mg Naloxone intranasal (i.n.) spray has early absorption rate that is comparable to intramuscular (i.m.) 0.4 mg injection and could be used as a take-home antidote. He suggests that high dose i.n. Naloxone could be given without risk of "overantagonism".

Jiten Ranchhodbhai Patel et al. discloses (Publication No. WO 2013093931—application PCT/IN20 12/00590, filed Sep. 6, 2012) a novel hydrazide group containing carbamates of naloxone.

Baohua Huang et al. describes in the article entitled "Human plasma-mediated hypoxic activation of indolequinone-based naloxone pro-drugs" (published in Bioorganic & Medicinal Chemistry Letters in 2009, 19(17), 5016-5020) that indolequinone based naloxone pro-drug can reverse opiate induced hypoxia.

I. Ukrainets et al. discloses in the publication Chemistry of Heterocyclic Compounds (2009), 45(4), pp. 405-416) studies of 3-O-acyl derivatives of naloxone as its potential prodrugs.

Xuemei Peng et al. describes in the article "Pharmacological Properties of Bivalent Ligands Containing Butorphan Linked to Nalbuphine and Nalaxone at μ, δ and κ Opioid Receptors" (published in the Journal of Medicinal Chemistry (May 2007), 50(9), 2254-2258) discloses bivalent ligands containing butorphan linked to naloxone.

I. Romanov et al. describes in the Russian Patent Publication (RU 2221566—published Jan. 20, 2004) that esters of N-substituted 14-hydroxymorphinans could be used as highly effective low toxic an antirelapse agent with prolonged opioprotective effect being after a single s.c. or i.m. injection.

I. Romanov et al. describes in the Russian Patent Publication (RU 2215741—published Nov. 10, 2003) the methods of preparation N-substituted 14-hydroxymorphinane esters.

Euro-Celtique, S. a., Chevchuk et al. describe in the Patent Publication No. WO 2003070191 (PCT/US/2003/004999—published Aug. 28, 2003) the methods of preventing pain with a tamper-resistant transdermal device containing 3-acyl-substituted antagonists.

Lu Zhengtang discloses in the Chinese Patent No. CN 1204649 (published Jan. 13, 1999) preparation of naloxone esters.

S. Lazar et al. describes in the article entitled "Synthesis and biological activity of the phosphate and sulfate esters of naloxone and naltrexone" (published in the European Journal of Medicinal Chemistry (1994), vol. 29(1), pp. 45-53) the synthesis and biological activity of the phosphate and sulfate esters of naloxone.

Hussein et al. describes (in Pharmaceutical Research (1988), vol. 5(9), pp. 615-18) that various prodrugs of naloxone where 3-phenoxy group is esterified lacked a bitter taste and had better buccal bioavailability in dogs.

Elie Gabriel Shami describes in European Patent Publication No. EP 170090 that benzoate ester prodrug derivatives of 3-hydroxymorphinans. The aforementioned publications are incorporated herein, as part of the specification.

None of these cited publications describes Naloxone combination with a hexadienoate included in the molecule, or indicates that such molecule will result and provide substantially more effective and long-lasting neutralizing/sobering effect when administered to a person.

DESCRIPTION OF INVENTION

The present invention involves a novel modification of opioids and their antagonists that leads to higher opioid receptor engagement when given orally. More specifically, the present invention involves modification of the appropriate opiate receptor modulators (e.g. Nalbuphine, Buprenorphine, Hydromorphine, Morphine, Pentazocine, Butorphanole, Naloxone, etc.) or related compounds to improve opiates' engagement of the opioid receptors when given orally.

The present invention further involves methods of mitigating opiate low oral bioavailability when opiates are used, without limitation, for the following conditions: pain management, palliative care, anesthesiology (e.g. postoperatively), skin disorders (e.g. pruritus), addictions (detox or management), certain locomotive disorders (e.g. levodopa-induced dyskinesias (LID) in Parkinson's disease, the dyskinesias associated with Tourette's syndrome, tardive dyskinesia, Huntington's disease, etc.

The present invention involves a novel modification of the opioid agent (e.g. Nalbuphine) that provides unexpected results of increasing the engagement of opioid receptors when given orally. Thus, this novel modification provides superior quality of care and allows for a wider range of therapeutic indications, including chronic conditions that require oral administration of the opioid.

The present invention involves a novel modification of the opioid antagonist, such as Naloxone combination with a hexadienoate included in the molecule, which provides substantially more effective and long-lasting neutralizing/sobering effect when administered to a person or patient.

The novel features of the present invention will be further described with reference to the following drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
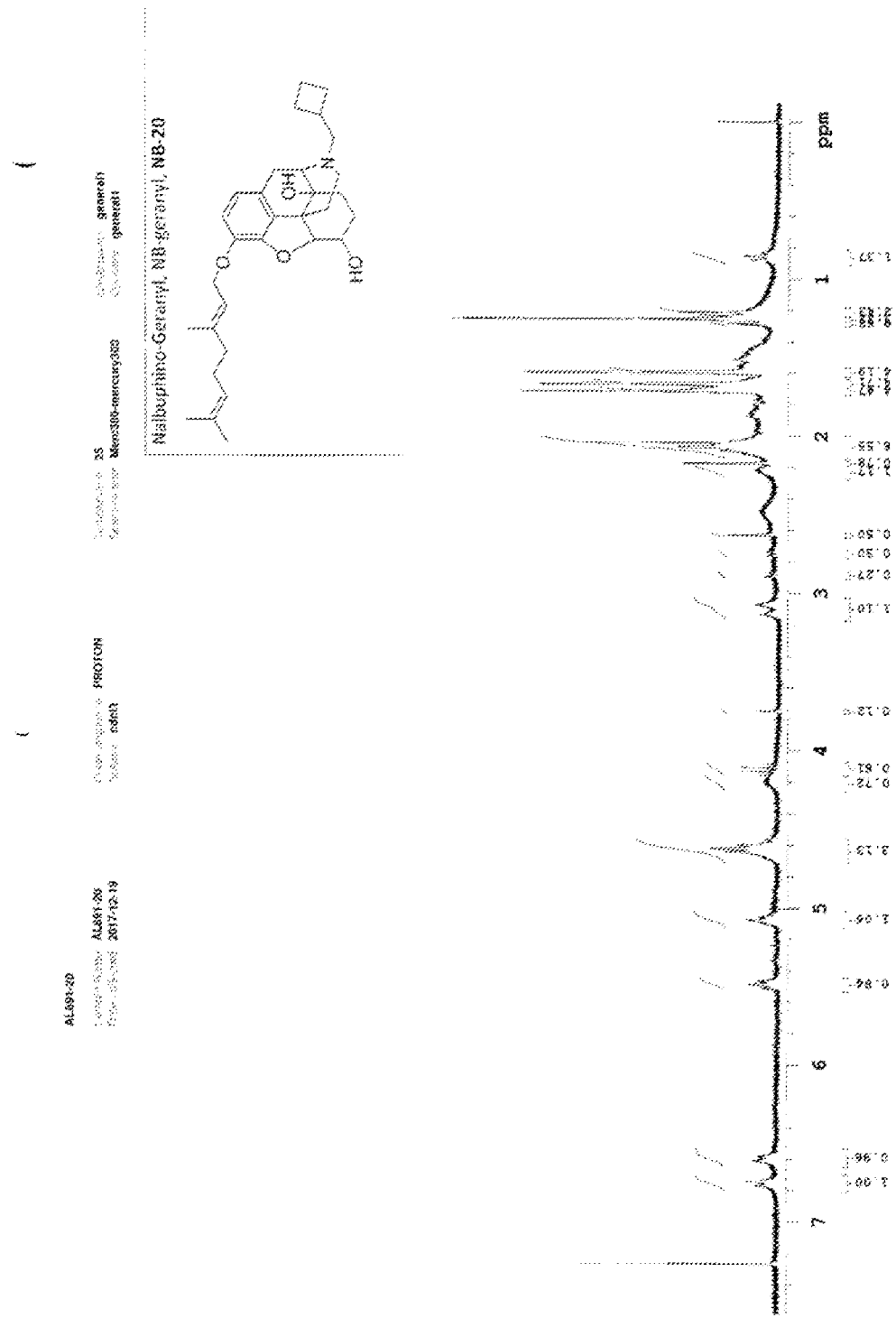
FIG. 1 illustrates NMR 1H spectrum of NB-20 compound, formulated in accordance with at least one embodiment of the present invention.
Figure 2:
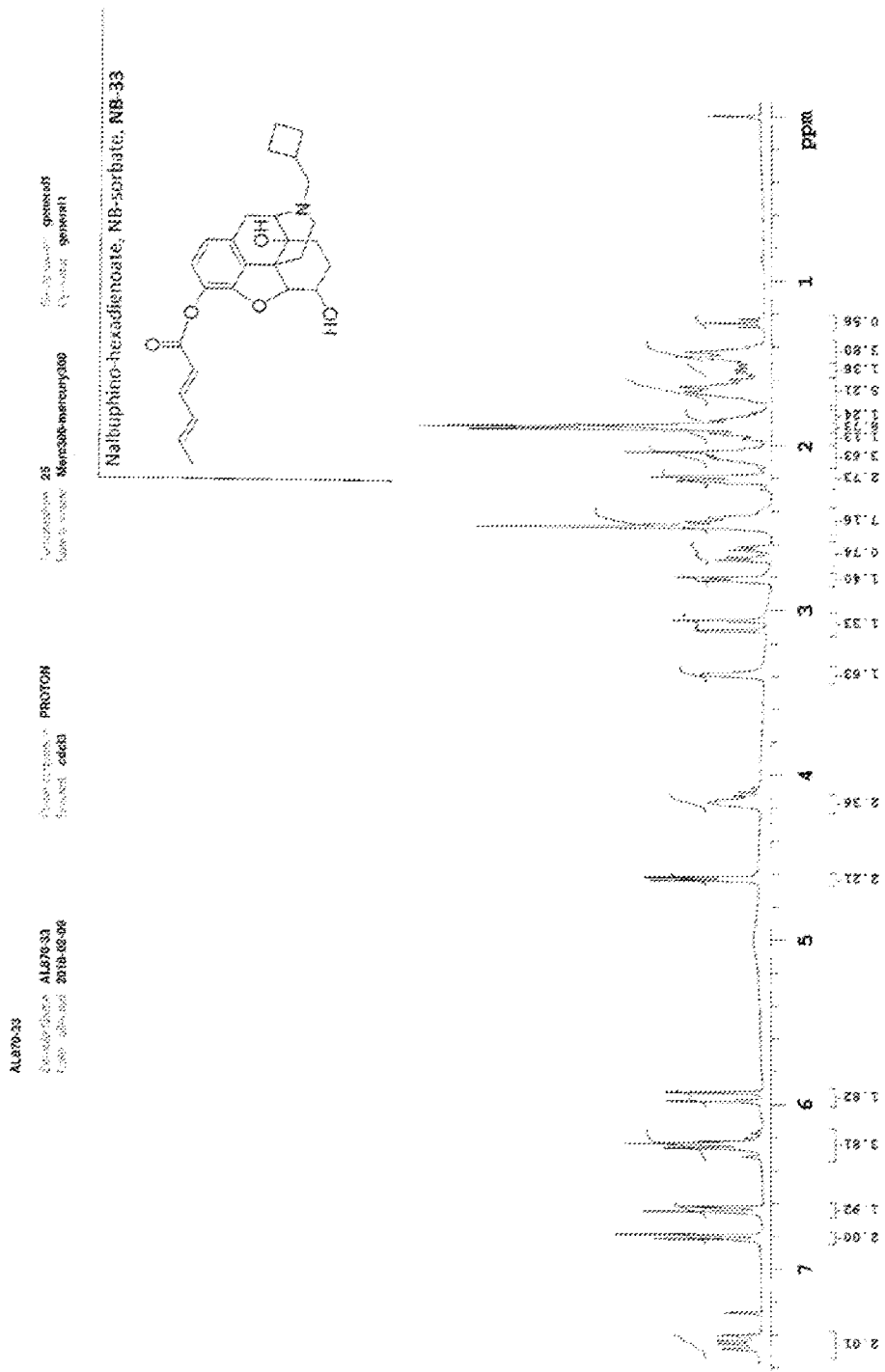
FIG. 2 illustrates NMR 1H spectrum of NB-33 compound, formulated in accordance with at least one embodiment of the present invention.
Figure 3:
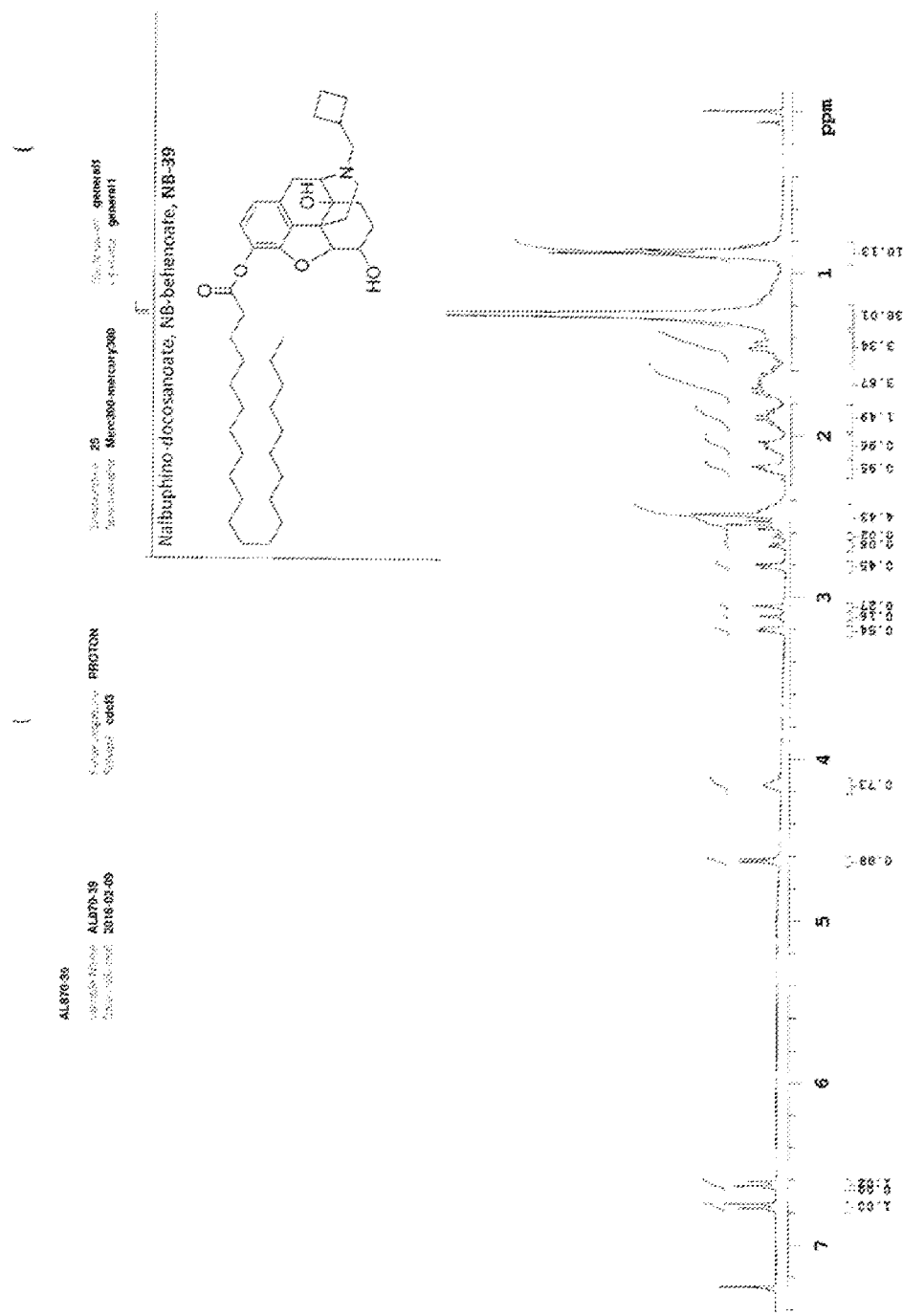
FIG. 3 illustrates NMR 1H spectrum of NB-39 compound, formulated in accordance with at least one embodiment of the present invention.
Figure 4:
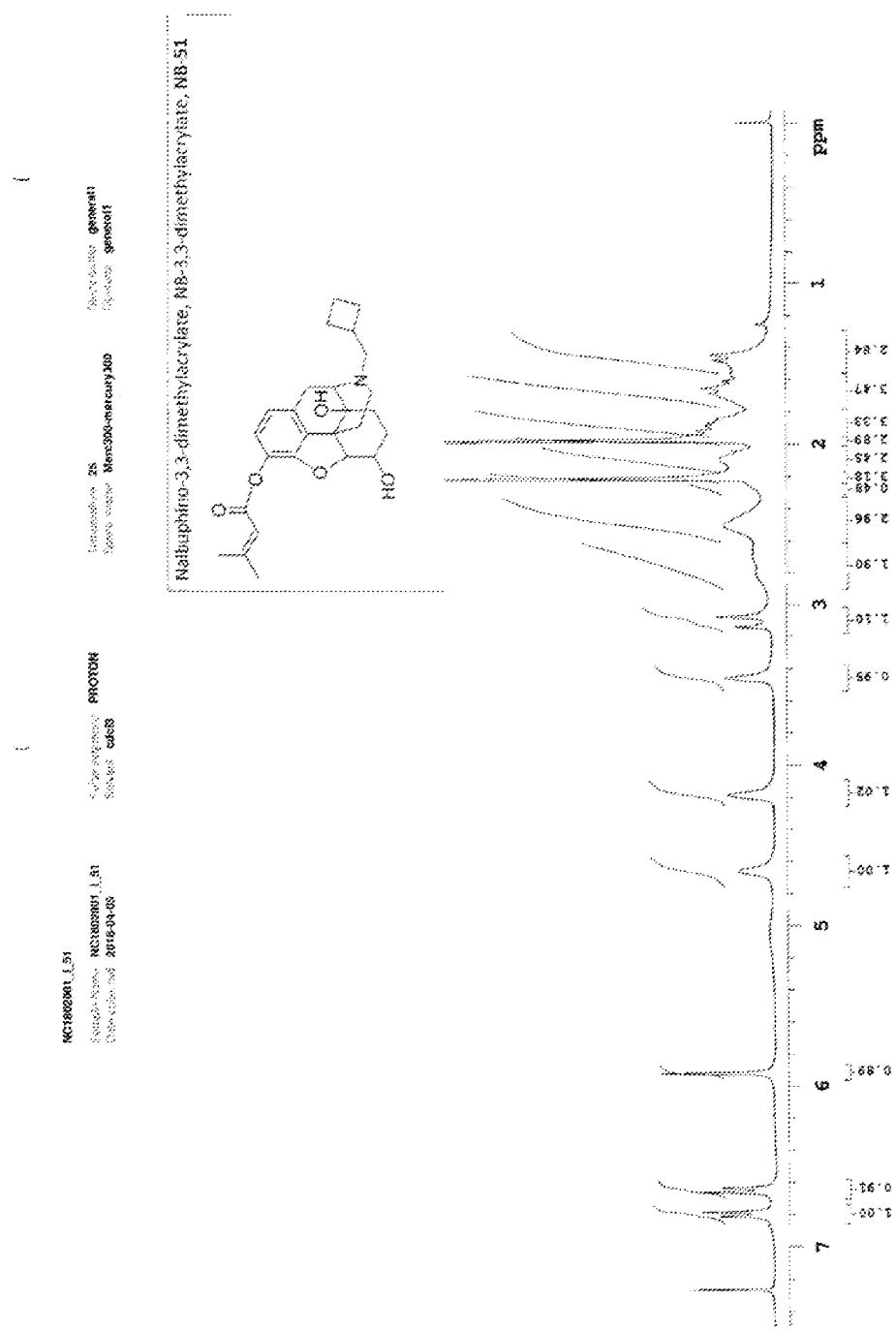
FIG. 4 illustrates NMR 1H spectrum of NB-51 compound, formulated in accordance with at least one embodiment of the present invention.
Figure 5:
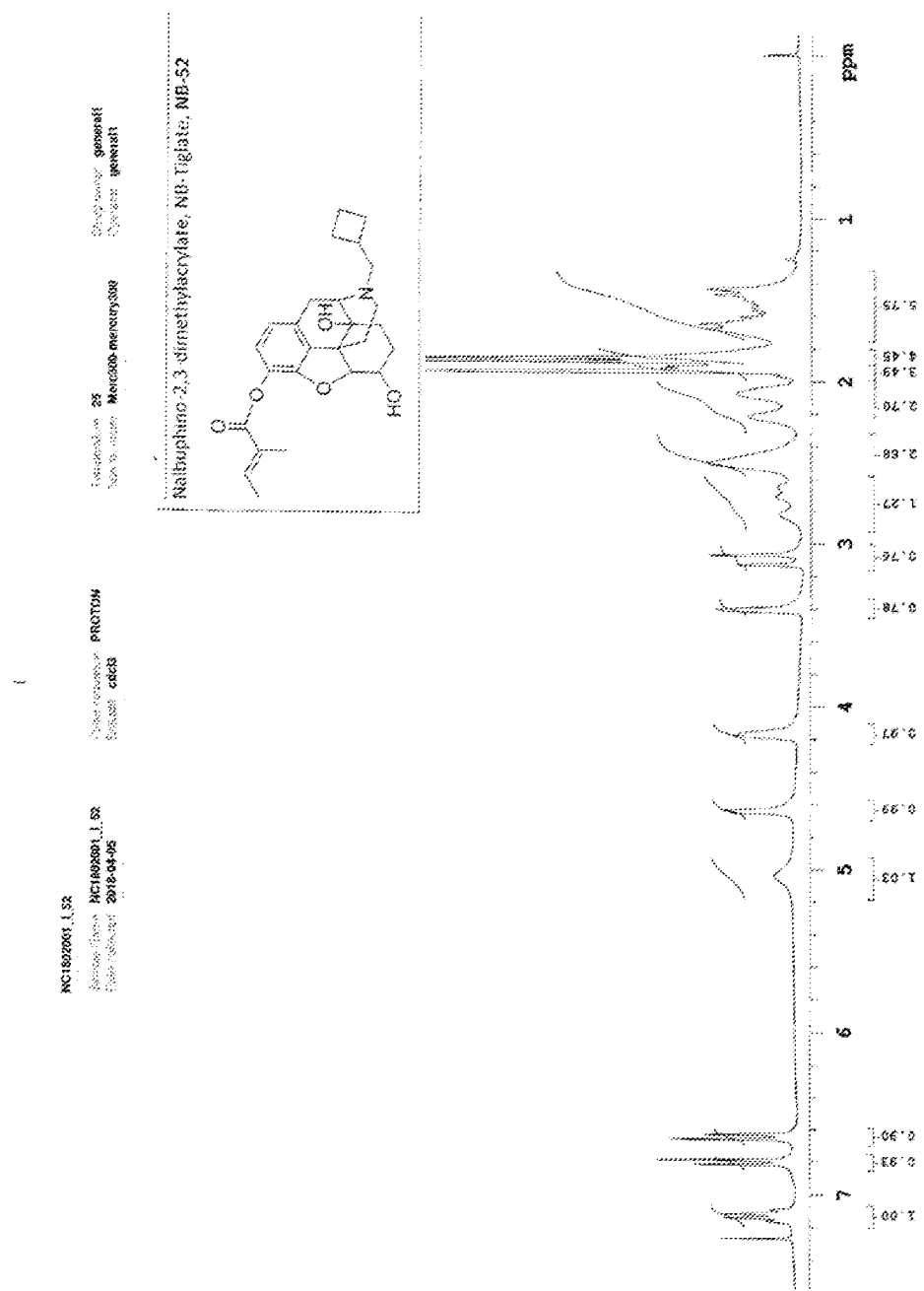
FIG. 5 illustrates NMR 1H spectrum of NB-52 compound, formulated in accordance with at least one embodiment of the present invention.
Figure 6:
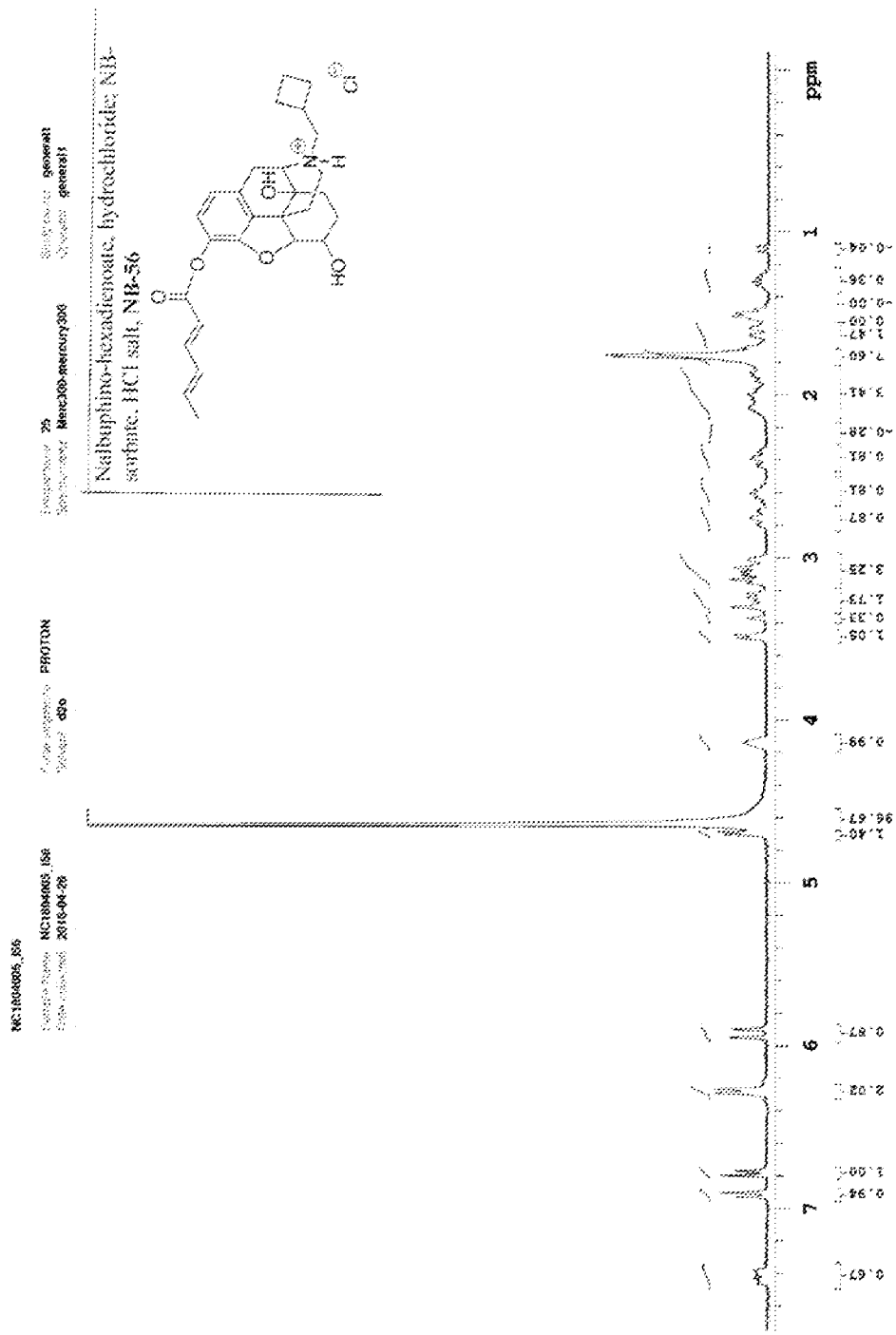
FIG. 6 illustrates NMR 1H spectrum of NB-56 compound, formulated in accordance with at least one embodiment of the present invention.
Figure 7:
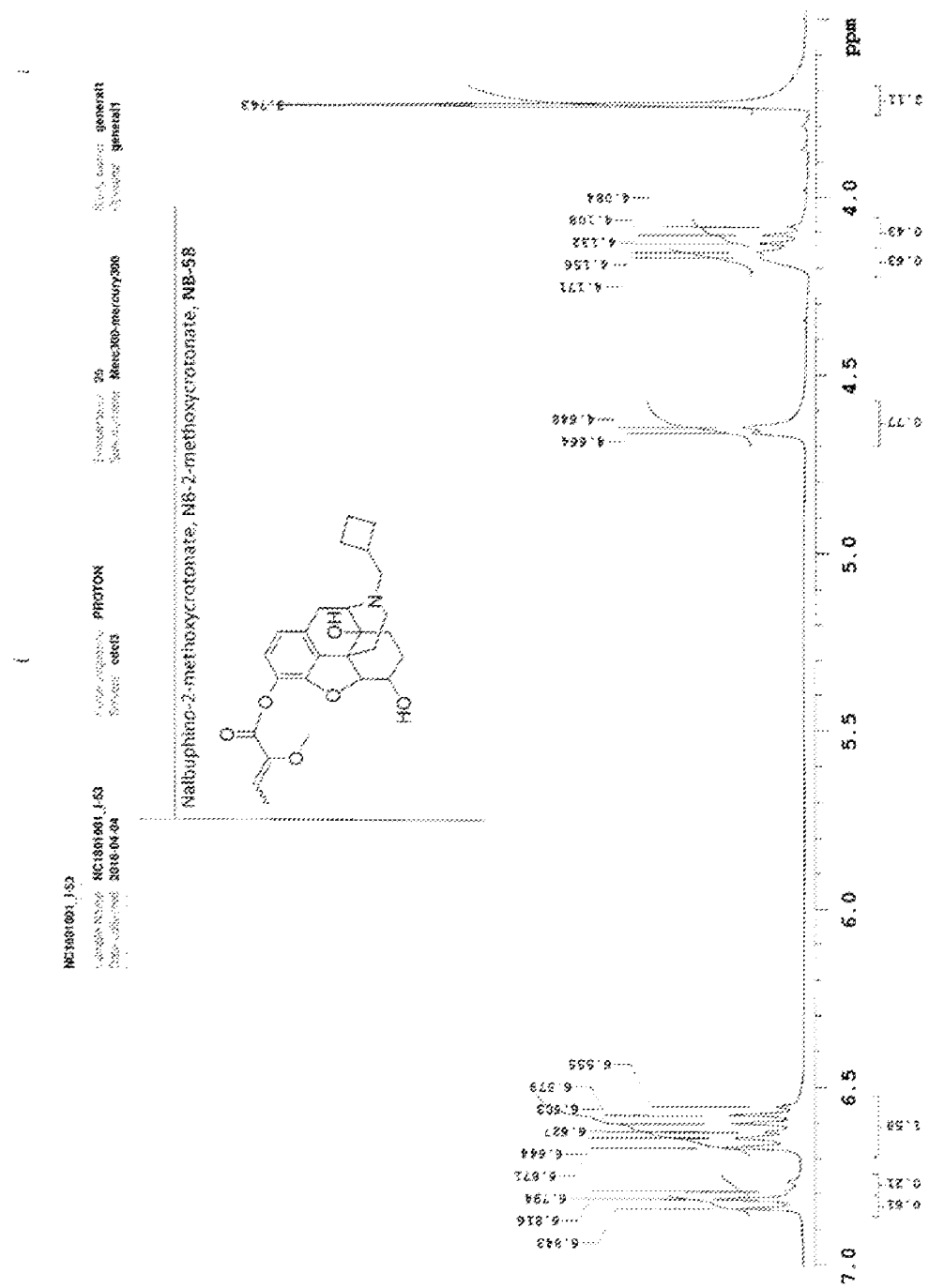
FIG. 7 illustrates NMR 1H spectrum of NB-58 compound, formulated in accordance with at least one embodiment of the present invention.
Figure 8:
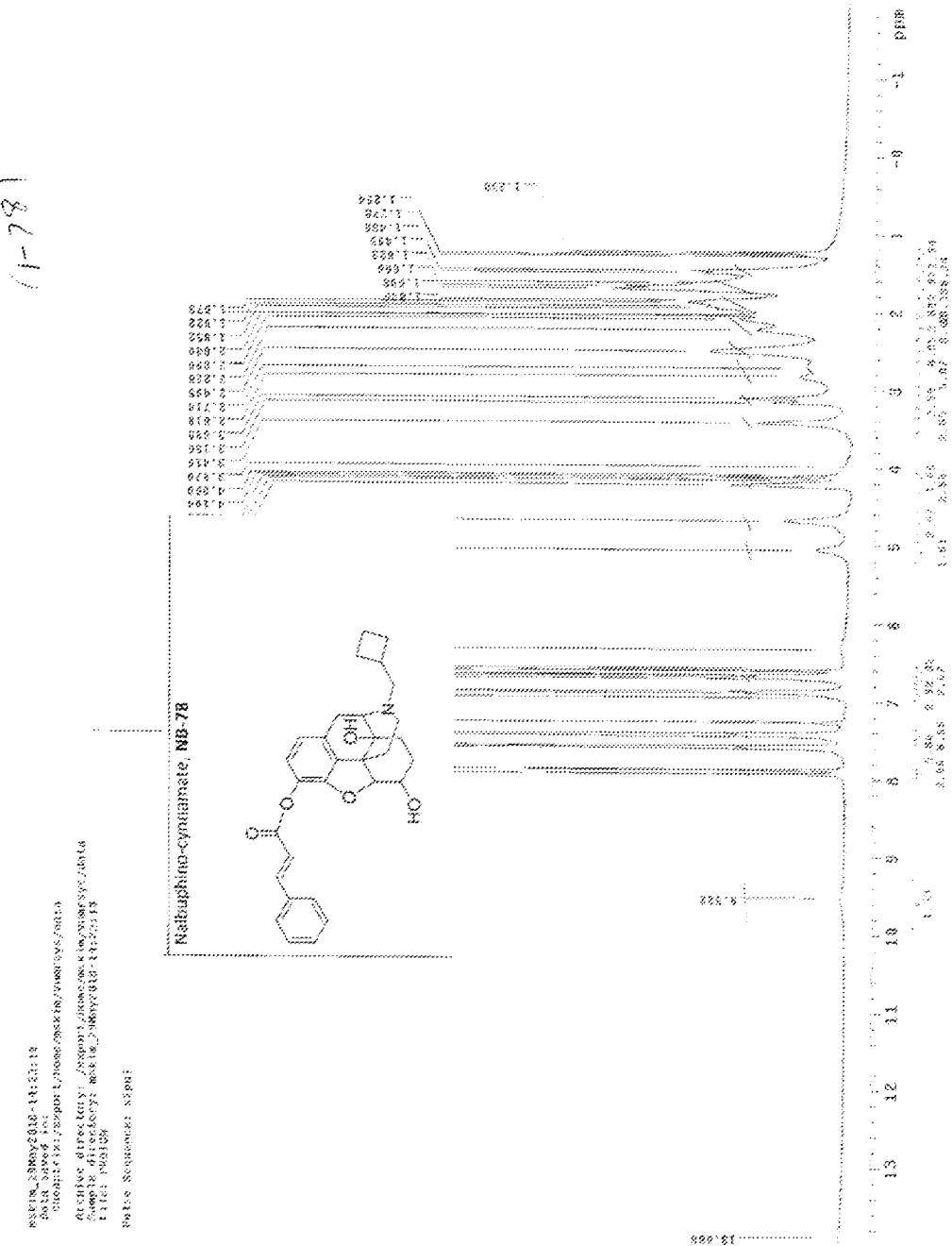
FIG. 8 illustrates NMR 1H spectrum of NB-78 compound, formulated in accordance with at least one embodiment of the present invention.

The present invention includes formation of an opiate derived compositions including hexadienoate and opioid residue in a single molecule, which is used in therapeutic areas associated with opioid receptor modulation.

The various aspects and features of the present invention and the composition is described with reference to TABLE 1, which illustrates the selected properties of compounds NB, NB-20, NB-28, NB-31, NB-32, NB-33, NB-39, NB-46, NB-51, NB-52, NB-56, NB-58, NB-76, NB-78.

Examples of NMR 1H spectrums of selected compounds (examples including NB-20, NB-33, NB-39, NB-51, NB-52, NB-56, NB-58, NB-78), formulated in accordance with at least one embodiment of the present invention are shown in FIGS. 1-8, respectively.

Surprisingly, 3-hexadienoate derivative of an opioid, created in accordance with at least one embodiment of the present invention, produced higher opioid receptor engagement than the parent opioid compound. Thus, for example, Nalbuphine 3-hexadienoate (NB-33) produced superior to the equivalent dose of both Nalbuphine 3-docosanoate (NB-39) and Nalbuphine (NB) analgesia in rats and humans, when given orally. Furthermore, a significant effect of NB-33 on pupil dilation (miosis) was observed in humans, which indicated superior receptor engagement.

Unexpectedly, when examining the effects of at least one embodiment of the present invention, was found that the position and the number of unsaturated sites of the ester of the phenoxy moiety is unique for hexadienic backbone and required for a superior engagement of opioid receptors. Thus, Nulbuphine 3-alkenoate (e.g. NB-33) produced better analgesia than the parent opioid, while other unsaturated acid derivatives of Nalbuphine (e.g. NB-31, NB-32, NB-52, or NB-78) produced no analgesia in rats.

Moreover, evaluating at least one embodiment of the present invention, it was found that Nalbuphine 3-hexadienoate has a unique and distinct opiate receptor signature of its own with human recombinant opiate receptors expressed in cells.

In accordance with at least one embodiment, the compounds of present invention comprise a general formula I or pharmaceutically acceptable salt of thereof

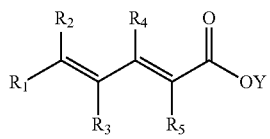

Formula I wherein $R_1$, $R_2$, $R_3$, $R_4$ or $R_5$ are selected from a group comprising H, optionally substituted C1-3 and OAlk), double bonds have E or Z geometry, and Y is an opioid residue.

In at least one embodiment, the present invention further relates to methods of mitigating opiate low oral bioavailability when opiates are used in the following, but not limited to, conditions: pain management, palliative care, anesthesiology (e.g. postoperatively), skin disorders (e.g. pruritus), addictions (detox or management), certain locomotive disorders (e.g. levodopa-induced dyskinesias (LID) in Parkinson's disease, and the dyskinesias associated with Tourette's syndrome, tardive dyskinesia and Huntington's disease, etc.

In at least one embodiment, the present invention is an optionally substituted hexadienoate of a phenoxy moiety modification of the appropriate opiate receptor modulators or related compounds to improve opiates' engagement of the opioid receptors when given orally.

In another embodiment, the present invention is a is an optionally substituted hexadienoate of a 3-phenoxy moiety modification of the appropriate opiate receptor modulators, including, but not limited to, Hydromorphine, Morphine, Nalbuphine, Pentazocine, Butorphanol, Buprenorphine, Naloxone or related compounds, formulated to improve opiates' engagement of the opioid receptors when given orally.

In at least one further embodiment, the present invention is a 3-hexadienoate modification of the appropriate opiate receptor modulators or related compounds, formulated to improve opiates' engagement of the opioid receptors when given orally.

In at least one embodiment, the present invention is a 3-hexadienoate modification of Nalbuphine or a pharmaceutically acceptable salt of thereof to improve engagement of the opioid receptors when given orally.

In yet another embodiment, the present invention is a 3-hexadienoate modification of Nalbuphine or a pharmaceutically acceptable salt of thereof to improve quality of pain management when given orally.

In a further one or more embodiments, the present invention is a 3-hexadienoate modification of Nalbuphine or a pharmaceutically acceptable salt of thereof to improve quality of pain management when given intravenously, intranasally, transdermally, sublingually, rectally, topically, intramuscularly, subcutaneously or via inhalation.

The following are further examples of compounds prepared in accordance with at least one embodiment of the present invention. The chemical name, composition and coding name for each of the compounds in Examples 1 is shown in TABLE 1 below.

Examples 1

(E)-3-(cyclobutylmethyl)-9-((3,7-dimethylocta-2,6-dien-1-yl)oxy)-1,2,3,4,5,6,7,7a-octahydro-4aH-4,12-methanobenzofuro[3,2-e]isoquinoline-4a,7-diol, Nalbuphino-Geranyl, (NB-20). Potassium bicarbonate (280 mg, 2.0 mmol) was added to suspension of nalbuphine hydrochloride (400 mg, 1.0 mmol) in acetone (20 mL) and toluene (20 mL) at room temperature. Geranyl bromide (320 mg, 1.5 mmol) was added. The reaction mixture was stirred under reflux for 4 h and overnight at room temperature. The reaction mixture was evaporated and the residue was purified by column chromatography (silicagel, EtOAc/Heptanes/MeOH, 1:1:0.10). The colorless oil was formed after evaporation of selected fractions, yield 45%, purity 91% by HPLC. The structure was confirmed by NMR $^1$H.

3-(cyclobutylmethyl)-9-(((2E,6E)-3,7,11-trimethyldodeca-2,6,10-trien-1-yl)oxy)-1,2,3,4,5,6,7,7a-octahydro-4aH-4,12-methanobenzofuro[3,2-e]isoquinoline-4a,7-diol, Nalbuphino-Farnesyl, (NB-28). This compound was prepared according to the procedure of NB-20, by substituting geranyl bromide for farnesyl bromide. The crude material was purified by column chromatography (silicagel, EtOAc/Heptanes, 1:1). The colorless oil was obtained after evaporation of selected fractions, yield 53%, purity 93% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl undec-10-enoate, Nalbuphino-undecelenoate, (NB-31). EDCI (1.04 g, 5.4 mmol) was added to undecylenic acid (1.0 g, 5.4 mmol) in THF (30 mL) at 0° C. with stirring. The reaction mixture was stirred for 10 min and Nalbuphine hydrochloride (2.13 g, 5.4 mmol), trimethylamine (1.1 g, 10.9 mmol) and 4-dimethylaminopyidine (0.22 g, 1.8 mmol) were added at 0° C. The stirring was continued for 1 h at 0° C. and at room temperature overnight. The reaction mixture was filtered, filtrate was evaporated, and the residue was purified by column chromatography (silicagel, EtOAc/Heptanes, 1:1). The white solid was formed after evaporation of selected fractions, yield 2.2 g (78%), purity 95% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl (E)-3,7-dimethylocta-2,6-dienoate, Nalbuphino-geranoate, (NB-32). This compound was prepared according to procedure of NB-31, by substituting undecylenic acid for geranyc acid. The crude material was purified by column chromatography (silicagel, EtOAc/Heptanes, 1:1). The white solid was formed after evaporation of selected fractions, yield 67%, and purity 96% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl (2E,4E)-hexa-2,4-dienoate, Nalbuphino-sorbate, (NB-33). EDCI (1.16 g, 6.1 mmol) was added to hexadienoic acid (0.68 g, 6.1 mmol) in THF (30 mL) at 0° C. with stirring. The reaction mixture was stirred for 10 min and Nalbuphine hydrochloride (2.39 g, 6.1 mmol), trimethylamine (1.2 g, 12 mmol) and 4-dimethylaminopyidine (0.25 g, 2 mmol) were added at 0° C. The stirring was continued for 1 h at 0° C. and at room temperature overnight. The reaction mixture was filtered, filtrate was evaporated, and the residue was purified by column chromatography (silicagel, EtOAc/Heptanes, 1:1). The white crystals were formed after evaporation of selected fractions, yield 2.05 g (75%), purity 98% by HPLC. The structure was confirmed by NMR $^1$H.

3-(cyclobutylmethyl)-9-(((2E,4E)-hexa-2,4-dienoyl)oxy)-4a,7-dihydroxy-2,3,4,4a,5,6,7,7a-octahydro-1H-4,12-methanobenzofuro[3,2-e]isoquinolin-3-ium chloride, Nalbuphino-sorbate, hydrochloride, (NB-56). HCl (gas) was bubbled into the solution of nalbuphino-sorbate (NB-33) (0.4 g, 0.89 mmol) in MTBE (15 mL) at 0° C. The white precipitate was formed immediately. The reaction mixture was stirred for 1 h and the solid was filtered, washed with MTBE and dried in vacuum. The yield 0.35 g (81%), purity 98% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl docosanoate, Nalbuphino-docosanoate, (NB-39). EDCI (0.56 g, 2.9 mmol) was added to behenic acid (1.0 g, 2.9 mmol) in THF (50 mL) at 0° C. with stirring. The reaction mixture was stirred for 30 min and Nalbuphine hydrochloride (1.16 g, 2.9 mmol), trimethylamine (0.29 g, 2.9 mmol) and 4-dimethylaminopyidine (0.12 g, 1.0 mmol) were added at 0° C. The stirring was continued for 1 h at 0° C. and at room temperature overnight. The reaction mixture was filtered, filtrate was evaporated, and the residue was purified by column chromatography (silicagel, EtOAc/Heptanes, 1:2). The white solid was formed after evaporation of selected fractions, yield 1.45 g (73%), purity 97% by HPLC. The structure was confirmed by NMR $^1$H. Synthesis and properties of NB-39 was also described in U.S. Pat. No. 5,750,534.

3-(cyclobutylmethyl)-4a,7-dihydroxy-2,3,4,4a,5,6,7,7a-octahydro-1H-4,12-methanobenzofuro[3,2-e]isoquinolin-9-yl isobutyrate, Nalbuphino-isobutyrate, NB-isovaleroate, (NB-46). This compound was prepared according to the procedure of NB-31, by substituting undecylenic acid for isovaleric acid. The crude material was purified by column chromatography (silicagel, EtOAc/Heptanes, 1:1). The white crystals were formed after evaporation of selected fractions, yield 54%, and purity 95% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl 3-methylbut-2-enoate, Nalbuphino-3,3-dimethylacrylate, (NB-51). This compound was prepared according to the procedure of NB-31, by substituting undecylenic acid for 3,3-dimethyl acrylic acid. The crude material was purified by column chromatography (silicagel, EtOAc/Heptanes, 1:1). The white crystals were formed after evaporation of selected fractions, yield 77%, purity 95% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl (E)-2-methylbut-2-enoate, Nalbuphino-2,3-dimethylacrylate, (52). This compound was prepared according to the procedure of NB-31, by substituting undecylenic acid for 2,3-dimethyl acrylic acid. The crude material was purified by column chromatography (silicagel, EtOAc/Heptanes, 1:1). The white crystals were formed after evaporation of selected fractions, yield 75%, purity 96% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl 2-methoxybut-2-enoate, Nalbuphino-2-methoxycrotonate, (NB-58). This compound was prepared according to the procedure of NB-31, by substituting undecylenic acid for 2-methoxy-crotonyc acid. The crude material was twice purified by column chromatography (silicagel, EtOAc/Heptanes, 1:1). The white oils were formed after evaporation of selected fractions, yield 27%, purity 94% by HPLC. The structure was confirmed by NMR $^1$H.

7-acetoxy-3-(cyclobutylmethyl)-4a-hydroxy-2,3,4,4a,5,6,7,7a-octahydro-1H-4,12-methanobenzofuro[3,2-e]isoquinolin-9-yl-(2E,4E)-hexa-2,4-dienoate, Nalbuphino-hexadienoate-acetate (NB-76). NB-33 (0.5 g, 1.1 mmol) was stirred in acetic anhydride (7.0 mL) at 40-50° C. overnight. EtOH (20 mL) was added and the reaction mixture was evaporated. The residue was twice purified by column chromatography (silicagel, EtOAc/Heptanes, 1:2). The white crystals were formed after evaporation of selected fractions, yield 1.45 g (50%), purity 97% by HPLC. The structure was confirmed by NMR $^1$H.

3-(cyclobutylmethyl)-4a,7-dihydroxy-2,3,4,4a,5,6,7,7a-octahydro-1H-4,12-methanobenzofuro[3,2-e]isoquinolin-9-yl cinnamate, Nalbuphino-cynnamate, (NB-78). This compound was prepared according to the procedure of NB-31, by substituting undecylenic acid for 2-trans-cynnamic acid. The crude material was purified by column chromatography (silicagel, EtOAc/Heptanes, 1:1). The white crystals were formed after evaporation of selected fractions, yield 67%, purity 94% by HPLC. The structure was confirmed by NMR $^1$H.

TABLE 1

| N | Name, Structure | Code | Stable in sGIF | Stable in plasma | Analgesia (rat) |
|---|---|---|---|---|---|
| 1 | Nalbuphine 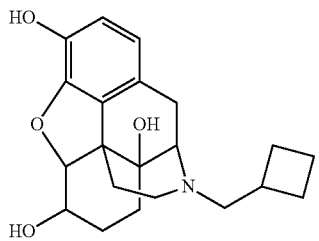 [SMILES: Oc1ccc2c3c1OC1C(O)CCC4(O)C(C2)N(CC2CCC2)CCC314] 3-(cyclobutylmethyl)-1,2,3,4,5,6,7,7a-octahydro-4aH-4,12-methanobenzofuro[3,2-e]isoquinoline-4a,7,9-triol<br>Chemical Formula: C21H27NO4<br>Molecular Weight: 357.45 | NB | n/a | n/a | moderate |
| 2 | Nalbuphino-Geranyl, NB-geranyl, 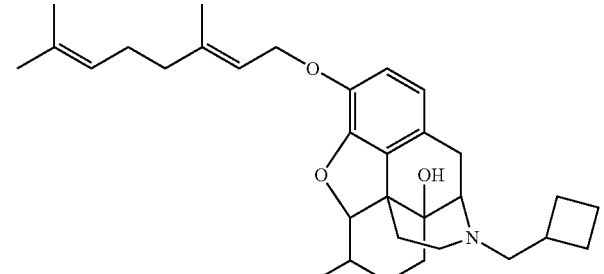 (E)-3-(cyclobutylmethyl)-9-((3,7-dimethylocta-2,6-dien-1-yl)oxy)-1,2,3,4,5,6,7,7a-octahydro-4aH-4,12-methanobenzofuro[3,2-e]isoquinoline-4a,7-diol<br>Chemical Formula: C31H43NO4<br>Molecular Weight: 493.69 | NB-20 | No | No | No |
| 3 | Nalbuphino-Farnesyl, NB-farnesyl, 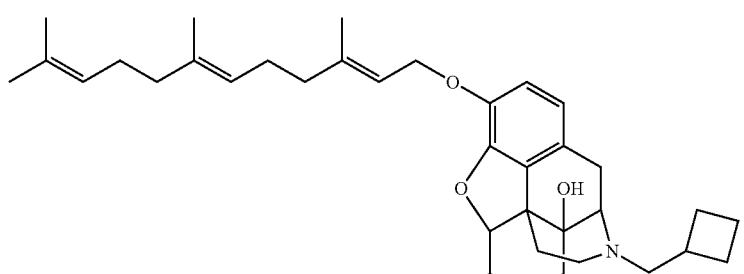 3-(cyclobutylmethyl)-9-(((2E,6E)-3,7,11-trimethyldodeca-2,6,10-trien-1-yl)oxy)-1,2,3,4,5,6,7,7a-octahydro-4aH-4,12-methanobenzofuro[3,2-e]isoquinoline-4a,7-diol<br>Chemical Formula: C36H51NO4<br>Molecular Weight: 561.81 | NB-28 | No | No | No |

TABLE 1-continued

| N | Name, Structure | Code | Stable in sGIF | Stable in plasma | Analgesia (rat) |
|---|---|---|---|---|---|
| 4 | Nalbuphino-undecelenoate | NB-31 | Yes | No | Inactive |

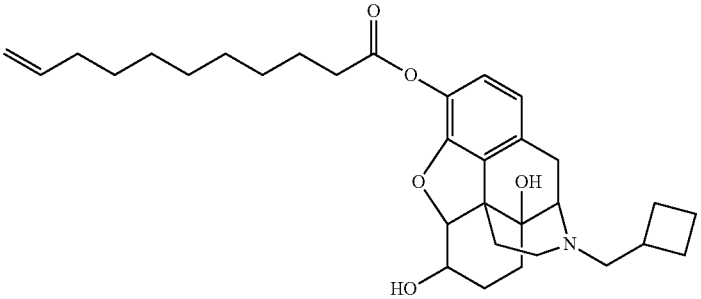 [SMILES: C=CCCCCCCCCC(=O)Oc1ccc2c3c1OC1C(O)CCC4(O)C(C2)N(CC2CCC2)CCC314]

3-(cyclobutylmethyl)-4a,7-dihydroxy-
2,3,4,4a,5,6,7,7a-
octahydro-1H-4,12-methanobenzofuro[3,2-
e]isoquinolin-9-yl undec-10-enoate
Chemical Formula: C32H45NO5
Molecular Weight: 523.71

| 5 | Nalbuphino-hexadienoate, NB-sorbate, | NB-33 | Yes | No | Excellent |

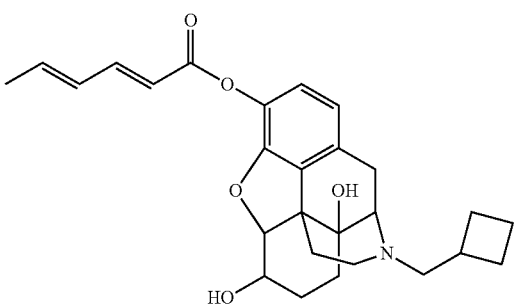 [SMILES: C/C=C/C=C/C(=O)Oc1ccc2c3c1OC1C(O)CCC4(O)C(C2)N(CC2CCC2)CCC314]

3-(cyclobutylmethyl)-4a,7-dihydroxy-
2,3,4,4a,5,6,7,7a-octahydro-1H-4,12-
methanobenzofuro[3,2-e]isoquinolin-9-yl (2E,4E)-
hexa-2,4-dienoate
Chemical Formula: C27H33NO5
Molecular Weight: 451.56

| 6 | Nalbuphino-hexadienoate, hydrochloride; NB-sorbate, HCl salt | NB-56 | Yes | No | No |

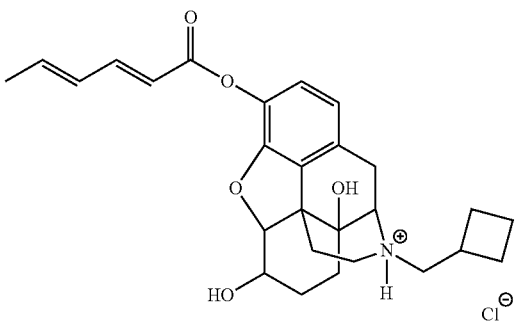 [SMILES: C/C=C/C=C/C(=O)Oc1ccc2c3c1OC1C(O)CCC4(O)C(C2)[NH+](CC2CCC2)CCC314 ; [Cl-]]

3-
(cyclobutylmethyl)-9-(((2E,4E)-hexa-2,4-
dienoyl)oxy)-4a,7-dihydroxy-2,3,4,4a,5,6,7,7a-
octahydro-1H-4,12-methanobenzofuro[3,2-
e]isoquinolin-3-ium chloride
Chemical Formula: C27H34ClNO5
Molecular Weight: 488.02

TABLE 1-continued

| N | Name, Structure | Code | Stable in sGIF | Stable in plasma | Analgesia (rat) |
|---|---|---|---|---|---|
| 7 | Nalbuphino-geranoate, NB-geranoate,<br>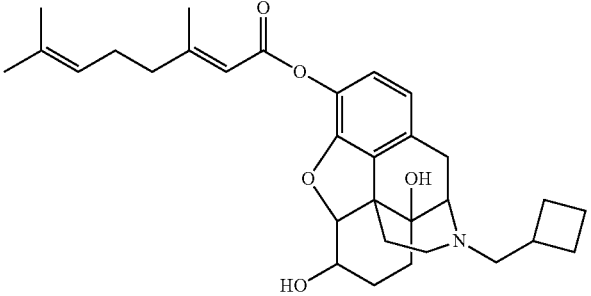 [SMILES: CC(C)=CCC/C(C)=C/C(=O)Oc1ccc2c3c1OC1C(O)CCC4(O)C(C2)N(CC2CCC2)CCC314]<br>3-(cyclobutylmethyl)-4a,7-dihydroxy-<br>2,3,4,4a,5,6,7,7a-octahydro-1H-4,12-<br>methanobenzofuro[3,2-e]isoquinolin-9-yl (E)-3,7-<br>dimethylocta-2,6-dienoate<br>Chemical Formula: C31H41NO5<br>Molecular Weight: 507.67 | NB-32 | Yes | No | Inactive |
| 8 | Nalbuphino-docosanoate, NB-behenoate,<br>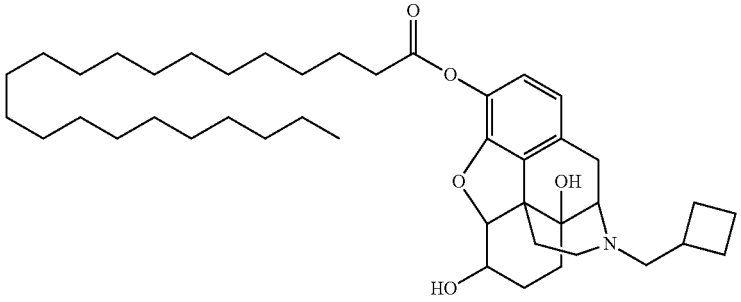 [SMILES: CCCCCCCCCCCCCCCCCCCCCC(=O)Oc1ccc2c3c1OC1C(O)CCC4(O)C(C2)N(CC2CCC2)CCC314]<br>3-(cyclobutylmethyl)-4a,7-dihydroxy-<br>2,3,4,4a,5,6,7,7a-octahydro-1H-4,12-<br>methanobenzofuro[3,2-e]isoquinolin-9-yl<br>docosanoate<br>Chemical Formula: C43H69NO5<br>Molecular Weight: 680.03 | NB-39 | Yes | No | Inactive |
| 9 | Nalbuphino-3,3-dimethylacrylate, NB-3,3-dimethylacrylate, NB-senecioate<br>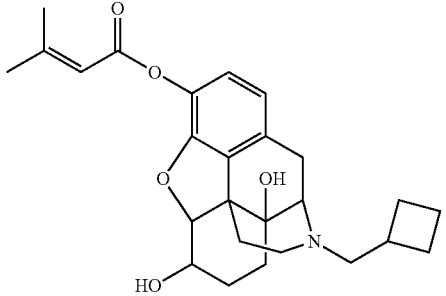 [SMILES: CC(C)=CC(=O)Oc1ccc2c3c1OC1C(O)CCC4(O)C(C2)N(CC2CCC2)CCC314]<br>3-(cyclobutylmethyl)-4a,7-dihydroxy-<br>2,3,4,4a,5,6,7,7a-octahydro-1H-4,12-<br>methanobenzofuro[3,2-e]isoquinolin-9-yl 3-<br>methylbut-2-enoate<br>Chemical Formula: C26H33NO5<br>Molecular Weight: 439.55 | NB-51 | Yes | No | Inactive |

TABLE 1-continued

| N | Name, Structure | Code | Stable in sGIF | Stable in plasma | Analgesia (rat) |
|---|---|---|---|---|---|
| 10 | Nalbuphino-2-methoxycrotonate, NB-2-methoxycrotonate 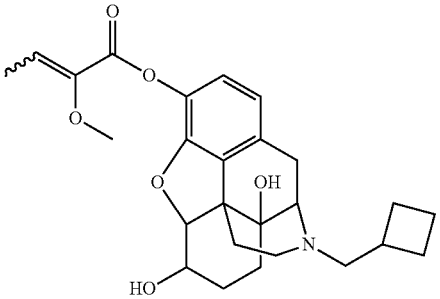 3-(cyclobutylmethyl)-4a,7-dihydroxy-2,3,4,4a,5,6,7,7a-octahydro-1H-4,12-methanobenzofuro[3,2-e]isoquinolin-9-yl 2-methoxybut-2-enoate<br>Chemical Formula: C26H33NO6<br>Molecular Weight: 455.55 | NB-58 | No | No | No |
| 11 | Nalbuphino-isobutyrate, NB-isovaleroate 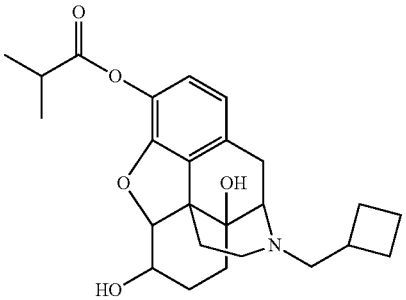 [SMILES: CC(C)C(=O)Oc1ccc2c3c1OC1C(O)CCC4(O)C(C2)N(CC2CCC2)CCC314] 3-(cyclobutylmethyl)-4a,7-dihydroxy-2,3,4,4a,5,6,7,7a-octahydro-1H-4,12-methanobenzofuro[3,2-e]isoquinolin-9-yl isobutyrate<br>Chemical Formula: C25H33NO5<br>Molecular Weight: 427.54 | NB-46 | Yes | Yes | No |
| 12 | Nalbuphino-2,3-dimethylacrylate, NB-Tiglate 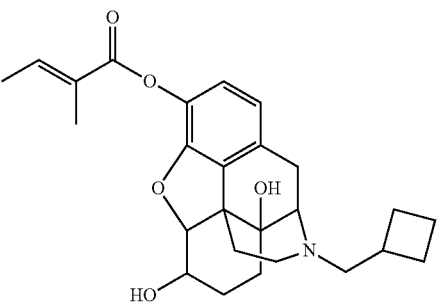 [SMILES: C/C=C(\C)C(=O)Oc1ccc2c3c1OC1C(O)CCC4(O)C(C2)N(CC2CCC2)CCC314] 3-(cyclobutylmethyl)-4a,7-dihydroxy-2,3,4,4a,5,6,7,7a-octahydro-1H-4,12-methanobenzofuro[3,2-e]isoquinolin-9-yl (E)-2-methylbut-2-enoate<br>Chemical Formula: C26H33NO5<br>Molecular Weight: 439.55 | NB-52 | Yes | No | Inactive |

TABLE 1-continued

| N | Name, Structure | Code | Stable in sGIF | Stable in plasma | Analgesia (rat) |
|---|---|---|---|---|---|
| 13 | Nalbuphino-hexadienoate-acetate, 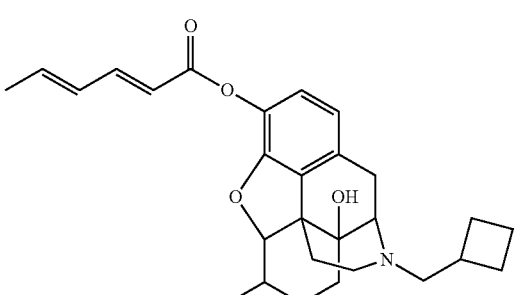 7-acetoxy-3-(cyclobutylmethyl)-4a-hydroxy-2,3,4,4a,5,6,7,7a-octahydro-1H-4,12-methanobenzofuro[3,2-e]isoquinolin-9-yl (2E,4E)-hexa-2,4-dienoate<br>Chemical Formula: C29H35NO6<br>Molecular Weight: 493.60 | NB-76 | Yes | No | moderate |
| 14 | Nalbuphino-cynnamate 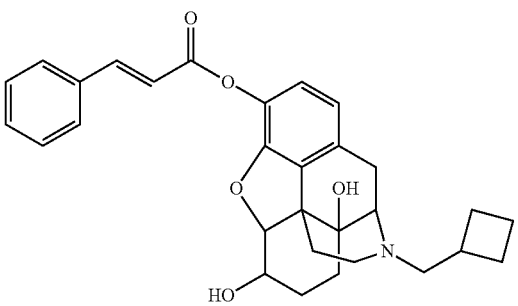 [SMILES: O=C(/C=C/c1ccccc1)Oc1ccc2c3c1OC1C(O)CCC4(O)C(C2)N(CC2CCC2)CCC314] 3-(cyclobutylmethyl)-4a,7-dihydroxy-2,3,4,4a,5,6,7,7a-octahydro-1H-4,12-methanobenzofuro[3,2-e]isoquinolin-9-yl cinnamate<br>Chemical Formula: C30H33NO5<br>Molecular Weight: 487.60 | NB-78 | Yes | No | Inactive |

Example 2—Stability in the Simulated Gastro-Intestinal Fluid (sGIF)

Stability of NB-33 in the simulated gastro-intestinal fluid (sGIF) was evaluated as below and individual compound data was summarized in Table 1.

sGIF is 0.5% solution of pepsine (Alfa Aesar, Pepsin, porcine stomach) in 0.1N aqueous HCl. Each derivative (50 mg) was mixed with sGIF (50 mL) and incubated at 37° C. on a shaker. The hydrolysis and release of Nalbuphine was monitored by HPLC at T=0 hr, 0.5 hr, 1 hr, 2 hr, and 4 hr. The acceptance criteria was defined as NLT 80% of the derivative still intact after 4 hrs.

Example 3—Stability in Human Plasma

Stability of NB-56 in human plasma was evaluated as below and the individual compound data was summarized in Table 1.

NB-56 (1.0 mg) was dissolved in 10 mL of plasma (Plasma Pooled Normal Human Plasma, Na-citrate, Innovative Research) with stirring for 10 min at 20° C. The solution was incubated at 37° C. 1 mL of solution was taken for each test sample. MeCN (0.05 mL) was added to sample solution. Shaking for 1 min followed by centrifugation (15 min, 14.000 r/m). Supernatant was filtered off and extracted with EtOAc (2×20 mL). The combined extract was dried over MgSO$_4$ and concentrated in vacuum. The residue was dissolved in MeOH (20 μL). The solution was used for HPLC injection.

The hydrolysis and release of Nalbuphine was monitored by HPLC at T=0 hr, 0.5 hr, 1 hr, 2 hr, and 4 hr. The acceptance criteria was defined as NLT than 20% of hydrolysis after 4 hrs.

Example 4

TABLE 2

Human recombinant opiate receptor data for NB-33

| Assay | NB-33 <1 uM | NB-33 >1 uM |
|---|---|---|
| mu (MOR) (h) (agonist effect) | | |
| mu (MOR) (h) (antagonist effect) | X | X |
| kappa (KOR) (h) (agonist effect) | | X |
| kappa (KOR) (h) (antagonist effect) | | |
| delta (DOR) (h) (agonist effect) | | X |
| delta (DOR) (h) (antagonist effect) | | |

Human recombinant opiate receptor (mu, kappa or delta) expressed in CHO-K1 cells were used. Test compound (NB-33)/or vehicle was incubated with the cells (4×10E5/mL) in modified HBSS pH 7.4 buffer at 370 C for 30 min. The reaction was evaluated for cAMP levels by TR-FRET. Compounds were screened at 0.3, 1 and 3 uM. by Eurofins Pharma Discovery Services.

Data for compound NB-33 is summarized in Table 2.

Example 5

Tests on Sprague-Dawley rats were conducted using Nalbuphine, NB-31, NB-32, NB-33, NB-33, NB39, NB-51, NB-52, NB-76 and NB-78.

Thirty Sprague-Dawley rats (12 week old; male) were randomly assigned to 10 groups and each group was gavaged with one of the following treatments: 1. Sesame oil; 2. Nalbuphine (in sesame oil; 60 uM/kg), 3. NB-31 (in sesame oil; 60 uM/kg), 4. NB-32 (in sesame oil; 60 uM/kg), 5. NB-33 (in sesame oil; 60 uM/kg), 6. NB-39 (in sesame oil; 60 uM/kg), 7. NB-51 (in sesame oil; 60 uM/kg), 8. NB-52 (in sesame oil; 60 uM/kg), 9. NB-76 (in sesame oil; 60 uM/kg), 10. NB-78 (in sesame oil; 60 uM/kg). Each rat received only one oral dose.

The antinociceptive activity was assessed as in Anesth Analg 2003; 97; 806-9 using the cold ethanol tail-flick test. The testing temperature was set at −20° C. and the cutoff time was 40 seconds. All rats were tested at T=0 immediately before medication. Measurements of the antinociceptive thresholds of saline, nalbuphine and nulbuphine derivatives were done at T=0 hr, 0.25 hr, 0.5 hr, 1 hr, 1.5 hr, 2 hr, 3 hr and 5 hr followed oral administration.

The data, as illustrated in the last column of Table 1 indicates excellent and superior results for NB-33.

Example 6

Double-blind, NB hydrochloride and NB-39 controlled, trial of the antinociceptive effect of oral NB-33 in healthy volunteers. Each of the three healthy volunteers was assigned a set of 6 non-transparent gelatin capsules as follows: 2×NB hydrochloride (MW=393.4; 39 mg), 2×NB-33 (MW=451.6; 45 mg) and 2×NB-39 (MW=680.0; 68 mg). Each week a healthy volunteer would receive a pill from the assigned set in a random fashion and take it orally. At T=0 hr, 0.25 hr, 0.5 hr, 1 hr, 1.5 hr, 2 hr, 3 hr and 5 hr followed oral administration a heat pain threshold was measured (hot water at 50° C.) as well as miosis.

Following one week of a wash out period, each volunteer repeated the protocol until all pills from the assigned set were administered. The individual data for heat pain threshold as % MPE=[(test latency−baseline latency)/(baseline latency)]×100 and for miosis as % MPE=[(test diameter−baseline diameter)/(baseline diameter)]×100 are shown in Table 2 and Table 3 respectively.

Tables 3, 4, and 5A-D illustrate that NB-33 resulted in analgesia and miosis superior to both the parent opioid NB and the parent opioid prodrug NB-39 when given orally. The differences in analgesia and miosis were statistically significant as indicated in Table 5A-D.

TABLE 3

| | % MPE (analgesia) | | | | | | | | |
|---|---|---|---|---|---|---|---|---|---|
| | 0 hr | 0.25 hr | 0.5 hr | 1 hr | 1.5 hr | 2 hr | 2.5 hr | 3 hr | 5 hr |
| 33 (45 mg) | 0.0 | 0.0 | 24.0 | 80.0 | 140.0 | 124.0 | 96.0 | 60.0 | 24.0 |
| 33 (45 mg) | 0.0 | 8.3 | 66.7 | 183.3 | 87.5 | 191.7 | 112.5 | 45.8 | 20.8 |
| 33 (45 mg) | 0.0 | 3.7 | 48.1 | 59.3 | 114.8 | 185.2 | 133.3 | 118.5 | 44.4 |
| 33 (45 mg) | 0.0 | 31.3 | 37.5 | 50.0 | 68.8 | 81.3 | 31.3 | 25.0 | 18.8 |
| 33 (45 mg) | 0.0 | 30.0 | 37.5 | 67.5 | 97.5 | 157.5 | 112.5 | 27.5 | 22.5 |
| 33 (45 mg) | 0.0 | 0.0 | 19.2 | 100.0 | 115.4 | 111.5 | 119.2 | 157.7 | 115.4 |
| NB (35 mg) | 0.0 | 0.0 | 5.6 | 50.0 | 100.0 | 94.4 | 66.7 | 22.2 | −5.6 |
| NB (35 mg) | 0.0 | 29.5 | 39.3 | 34.4 | 54.1 | 54.1 | 82.0 | 32.8 | 27.9 |
| NB (35 mg) | 0.0 | 5.3 | 10.5 | 42.1 | 68.4 | 94.7 | 57.9 | 68.4 | 5.3 |
| NB (35 mg) | 0.0 | 56.3 | 50.0 | 87.5 | 112.5 | 162.5 | 106.3 | 37.5 | 26.7 |
| NB (35 mg) | 0.0 | 5.3 | 21.1 | 47.4 | 73.7 | 57.9 | 36.8 | 57.9 | 5.3 |
| NB (35 mg) | 0.0 | 21.4 | 35.7 | 57.1 | 78.6 | 50.0 | 35.7 | 0.0 | 0.0 |
| 39 (68 mg) | 0.0 | 0.0 | 10.0 | 10.0 | 15.0 | 10.0 | 5.0 | 10.0 | 0.0 |
| 39 (68 mg) | 0.0 | 17.6 | 11.8 | 5.9 | 11.8 | 23.5 | 0.0 | 11.8 | 0.0 |
| 39 (68 mg) | 0.0 | 13.3 | 40.0 | 73.3 | 93.3 | 93.3 | 46.7 | 40.0 | 6.7 |
| 39 (68 mg) | 0.0 | 6.2 | 6.2 | 10.8 | −7.7 | 33.8 | −6.2 | 9.2 | −9.2 |
| 39 (68 mg) | 0.0 | 8.3 | 55.6 | 11.1 | 19.4 | 0.0 | 16.7 | 0.0 | −2.8 |
| 39 (68 mg) | 0.0 | 0.0 | 15.0 | 5.0 | 5.0 | 0.0 | 5.0 | 0.0 | 5.0 |

TABLE 4

| | % MPE (miosis) | | | | | | | | |
|---|---|---|---|---|---|---|---|---|---|
| | 0 hr | 0.25 hr | 0.5 hr | 1 hr | 1.5 hr | 2 hr | 2.5 hr | 3 hr | 5 hr |
| 33 (45 mg) | 0.0 | −8.8 | 3.4 | 24.0 | 20.6 | 37.8 | 46.4 | 3.4 | 3.4 |
| 33 (45 mg) | 0.0 | 0.3 | 26.7 | 40.4 | 36.5 | 46.2 | 63.7 | 36.5 | 36.5 |
| 33 (45 mg) | 0.0 | 20.0 | 33.3 | 42.2 | 42.2 | 42.2 | 29.5 | 15.6 | 9.3 |
| 33 (45 mg) | 0.0 | 0.0 | −6.3 | 33.9 | 33.9 | 42.9 | 33.9 | 25.0 | 17.2 |
| 33 (45 mg) | 0.0 | −5.0 | 26.7 | 26.7 | 36.5 | 46.2 | 46.2 | 36.5 | 33.7 |
| 33 (45 mg) | 0.0 | 26.7 | 26.7 | 40.4 | 46.2 | 55.9 | 65.7 | 29.0 | 32.1 |
| NB (35 mg) | 0.0 | 3.1 | 9.4 | 21.9 | 17.2 | 18.8 | 18.8 | 6.2 | 6.2 |
| NB (35 mg) | 0.0 | 9.4 | 37.5 | 46.9 | 65.6 | 31.3 | 3.1 | 6.2 | 3.1 |
| NB (35 mg) | 0.0 | 6.7 | 0.0 | 6.7 | 25.0 | 55.6 | 50.0 | 33.3 | 22.2 |
| NB (35 mg) | 0.0 | 0.0 | 9.4 | 21.9 | 17.2 | 31.3 | 25.0 | 21.9 | 6.2 |
| NB (35 mg) | 0.0 | 3.2 | 9.7 | 45.2 | 45.2 | 58.1 | 25.8 | 16.1 | 9.7 |
| NB (35 mg) | 0.0 | 2.9 | 8.8 | −2.9 | 29.4 | 11.8 | 26.5 | 20.6 | 7.8 |
| 39 (68 mg) | 0.0 | 10.3 | 14.9 | 37.9 | 37.9 | 14.9 | 14.9 | 24.1 | 3.4 |
| 39 (68 mg) | 0.0 | 0.0 | 0.0 | 6.7 | 6.7 | 0.0 | 6.7 | 0.0 | 0.0 |
| 39 (68 mg) | 0.0 | 25.0 | 16.7 | 22.2 | 33.3 | 25.0 | 11.1 | 11.1 | 11.1 |
| 39 (68 mg) | 0.0 | 12.5 | 9.4 | 18.8 | 21.9 | 17.2 | 6.2 | 0.0 | 0.0 |
| 39 (68 mg) | 0.0 | 20.0 | 26.7 | 36.7 | 23.3 | 16.7 | 13.3 | 3.3 | 13.3 |
| 39 (68 mg) | 0.0 | 3.1 | 9.4 | 21.9 | 25.0 | 6.2 | 9.4 | 0.0 | 3.1 |

Independent samples t-test was used to compare the means of % MPE analgesia and miosis in the two pairs of samples: NB-33 and NB and NB-33 and NB-39. All analyses were made using SPSS (v.25).

Bold indicates statistical significance at $\alpha=0.05$

Tables 5A-D illustrate comparison of analgesia and miosis between NB-33 and NB, NB-39.

TABLE 5A

Analgesia, NB-33 vs. NB

| hrs | T | p-value |
|---|---|---|
| 0.25 | −.705 | .497 |
| 0.5 | 1.182 | .264 |
| 1 | 1.730 | .114 |
| 1.5 | 1.699 | .120 |
| 2 | 2.258 | .048 |
| 2.5 | 1.982 | .076 |
| 3 | 1.486 | .168 |
| 5 | 1.895 | .087 |

TABLE 5B

Analgesia, NB-33 vs. NB-39

| hrs | t | p-value |
|---|---|---|
| 0.25 | .700 | .506 |
| 0.5 | 1.467 | .173 |
| 1 | 3.110 | .011 |
| 1.5 | 4.558 | .001 |
| 2 | 5.027 | .001 |
| 2.5 | 5.380 | .000 |
| 3 | 2.656 | .039 |
| 5 | 2.642 | .025 |

TABLE 5C

Miosis, NB-33 vs. NB

| hrs | t | p-value |
|---|---|---|
| 0.25 | .217 | .836 |
| 0.5 | .716 | .491 |
| 1 | 1.295 | .224 |
| 1.5 | .318 | .757 |

TABLE 5C-continued

Miosis, NB-33 vs. NB

| hrs | t | p-value |
|---|---|---|
| 2 | 1.328 | .232 |
| 2.5 | 2.624 | .025 |
| 3 | 1.022 | .331 |
| 5 | 2.018 | .071 |

TABLE 5D

Miosis, NB-33 vs. NB-39

| hrs | t | p-value |
|---|---|---|
| 0.25 | −.893 | .393 |
| 0.5 | .751 | .470 |
| 1 | 1.843 | .095 |
| 1.5 | 1.985 | .075 |
| 2 | 7.253 | .000 |
| 2.5 | 5.982 | .001 |
| 3 | 2.713 | .022 |
| 5 | 2.732 | .031 |

Table 6A and Graph 1 in FIG. 13 below illustrate additional testing results for the NB-33 on Randall-Selitto rats, demonstrating its efficacy and benefits (including greater stability) in comparison to base compound.

Table 6A and Graph 1 in FIG. 13 below illustrate additional testing results for the NB-33 on Randall-Selitto rats, demonstrating its efficacy and benefits (including greater stability) in comparison to base compound.

TABLE 6A

WO# 10656913 AB137003
Species/Strain/Sex: Rate

| Treatment | Route | Dose | No. | Randall-Selitto (g) | | | | | |
|---|---|---|---|---|---|---|---|---|---|
| | | | | Pre-treatment | \multicolumn{5}{c}{Post-dose} | | | | |
| | | | | | 0.5 hr | 1 hr | 2 hr | 4 hr | 6 hr |
| Vehicle (0.9% NaCl) | SC | 5 mL/kg | 1 | 92 | 73 | 98 | 92 | 65 | 75 |
| | | | 2 | 97 | 68 | 88 | 72 | 69 | 62 |
| | | | 3 | 86 | 68 | 76 | 92 | 97 | 97 |
| | | | 4 | 91 | 86 | 82 | 77 | 83 | 53 |
| | | | 5 | 83 | 91 | 57 | 69 | 64 | 61 |
| | | | Mean | 89.8 | 77.2 | 80.2 | 80.4 | 75.6 | 69.6 |
| | | | SEM | 2.4 | 4.8 | 6.8 | 4.9 | 6.3 | 7.7 |
| PT#1225608 AFC-2 NB.HCl | SC | 3 mg/kg | 1 | 89 | 78 | 63 | 58 | 64 | 50 |
| | | | 2 | 92 | 89 | 62 | 71 | 66 | 71 |
| | | | 3 | 100 | 93 | 92 | 103 | 93 | 82 |
| | | | 4 | 80 | 107 | 90 | 69 | 93 | 69 |
| | | | 5 | 91 | 134 | 96 | 93 | 61 | 85 |
| | | | Mean | 90.4 | 100.2 | 80.6 | 78.8 | 75.4 | 71.4 |
| | | | SEM | 3.2 | 9.6 | 7.5 | 8.3 | 7.2 | 6.2 |
| PT#1225607 AFC-1 NB-33.HCl | SC | 3.9 mg/kg | 1 | 93 | 121 | 98 | 99 | 83 | 79 |
| | | | 2 | 82 | 120 | 103 | 94 | 71 | 64 |
| | | | 3 | 98 | 207 | 199 | 214 | 136 | 101 |
| | | | 4 | 80 | 161 | 73 | 102 | 63 | 65 |
| | | | 5 | 96 | 96 | 86 | 85 | 97 | 85 |
| | | | Mean | 89.8 | 141.0\* | 111.8 | 118.8 | 90.0 | 78.8 |
| | | | SEM | 3.7 | 19.5 | 22.4 | 24.0 | 12.9 | 6.9 |

Figure 13:
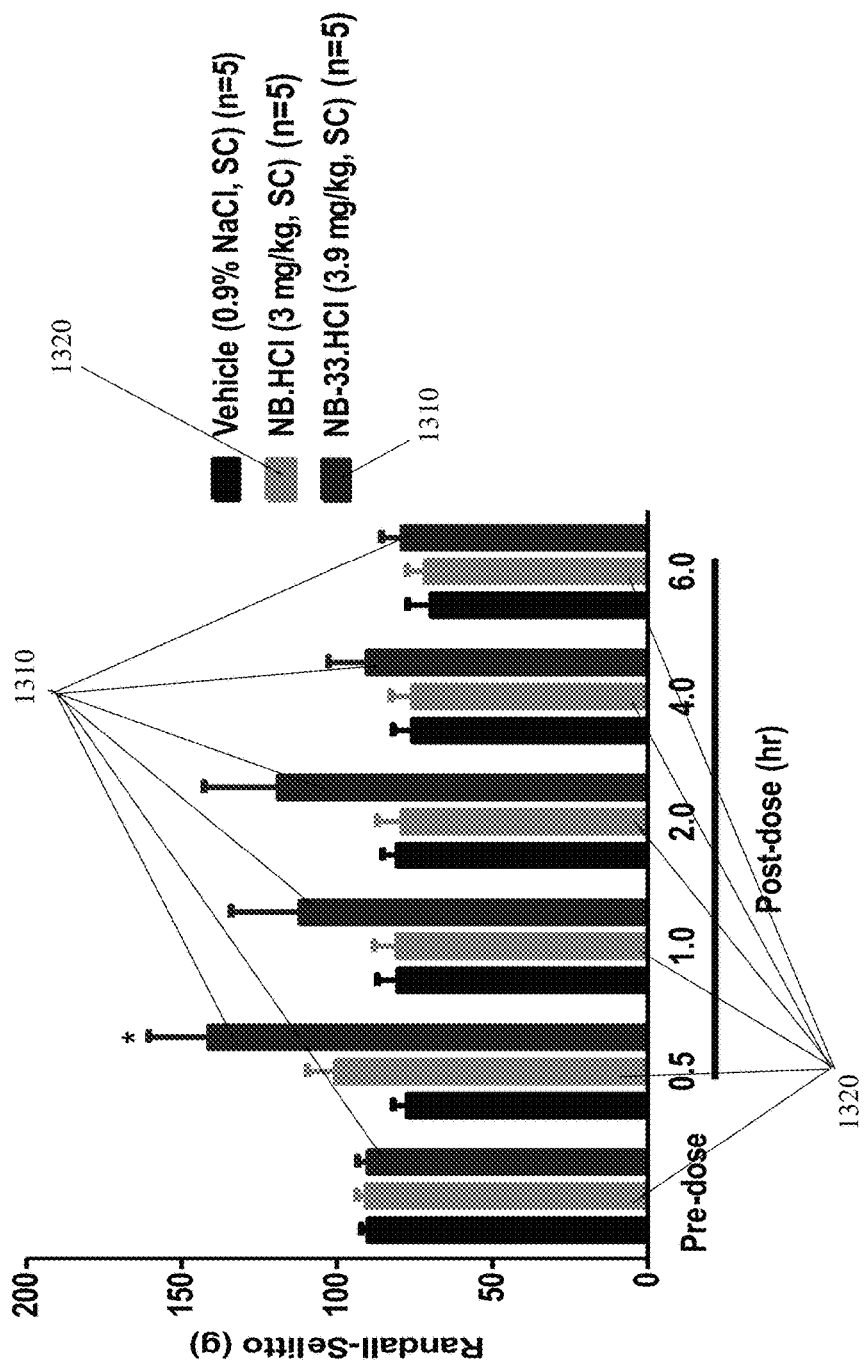
FIG. 13 shows Graph 1, illustrating superior analgesic properties of the NB-33, according to at least one embodiment, in comparison to the equimolar dose of the parent opioid NB.

The data on the Graph 1 in FIG. 13 shows that NB-33 has superior analgesic properties to the equimolar dose of the parent opioid NB. FIG. 13 illustrate in the graphical form the results for 1310 NB-33, marked 1310, in comparison to the base NB compound NB, marked 1320 in FIG. 13.

Example 7

This invention is exemplified by but not limited to the following compounds, illustrated below. The following compounds, shown in TABLE 7 below, provide non-limiting examples of various opioids, modified by hexadienoate in accordance with at least one embodiment.

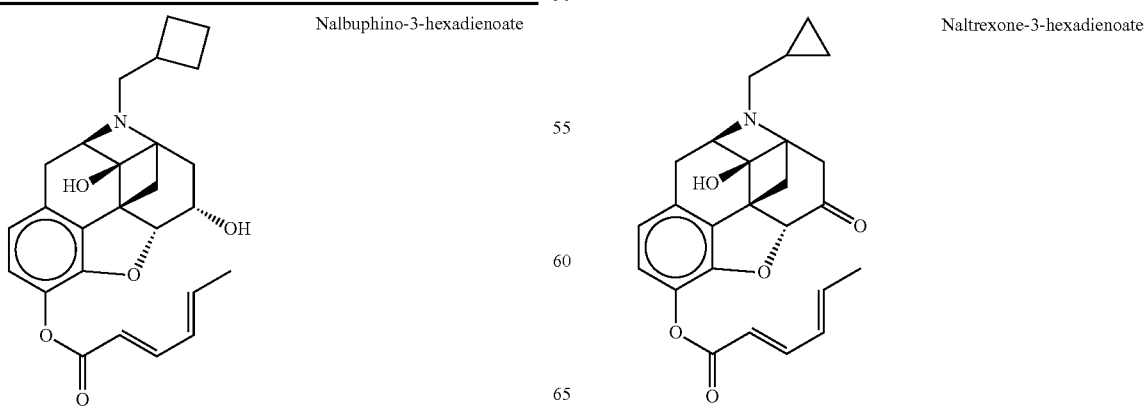

TABLE 7 — Nalbuphino-3-hexadienoate

TABLE 7-continued — Naloxone-3-hexadienoate

Naltrexone-3-hexadienoate

TABLE 7-continued
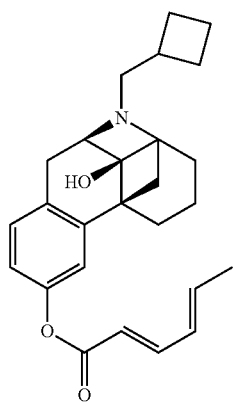
Butorphanolo-3-hexadienoate
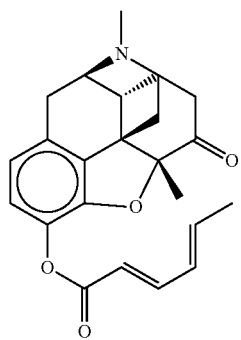
Metopon hexadienoate
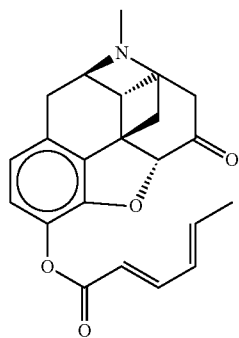
Hydromorphone hexadienoate
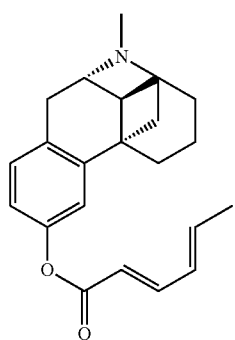
Levorphanol hexadienoate
TABLE 7-continued
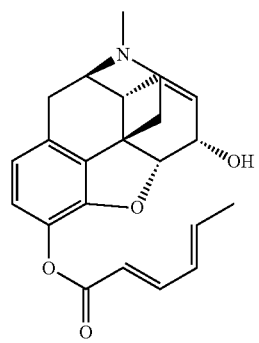
Morphino-3-hexadienoate
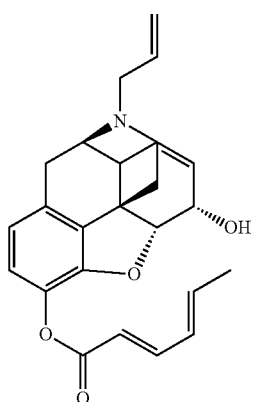
Nalorphino-3-hexadienoate
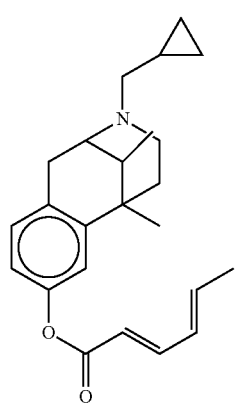
Cyclazocine hexadienoate
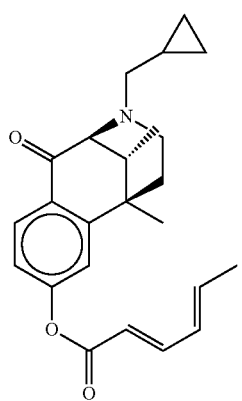
Ketocyclazocine hexadienoate TABLE 7-continued
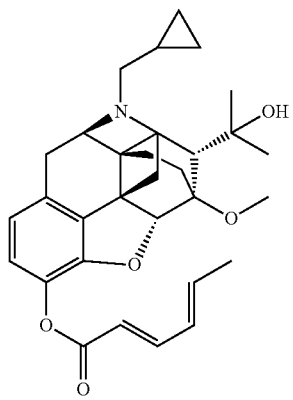
Diprenorphine hexadienoate
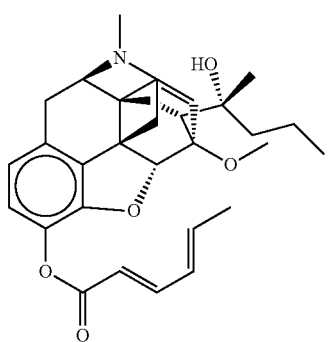
Etorphine hexadienoate
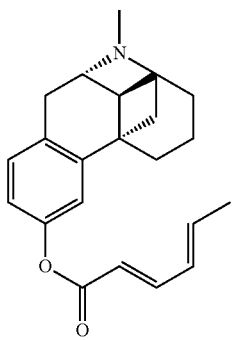
Levorphanol hexadienoate
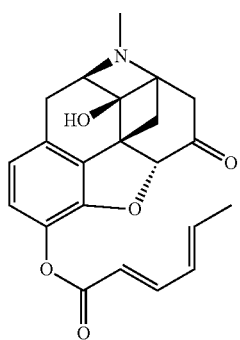
Oxymorphone hexadienoate
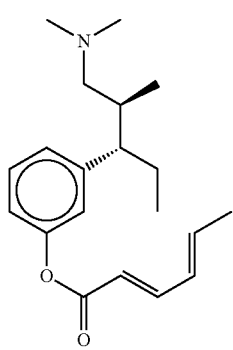
Tapentadol hexadienoate
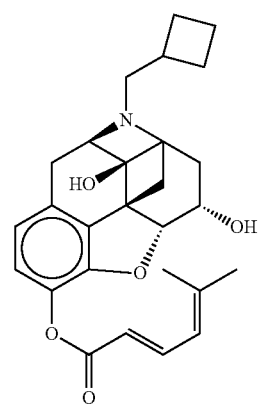
Nalbuphino-3-(5-methyl)hexadienoate
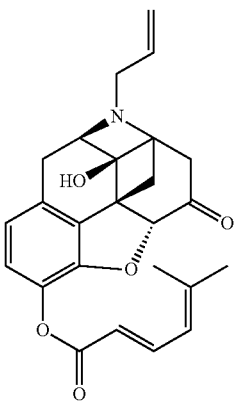
Naloxone-3-(5-methyl)hexadienoate
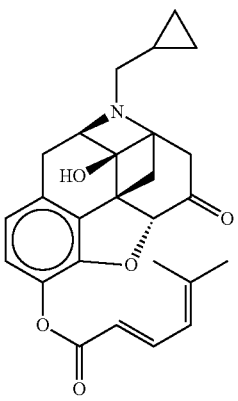
Naltrexone-3-(5-methyl)hexadienoate TABLE 7-continued
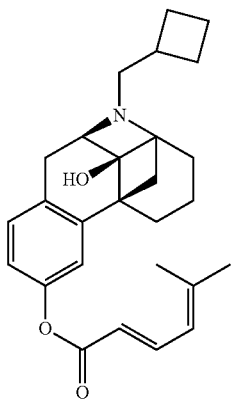
Butorphanolo-3-
(5-methyl)hexadienoate
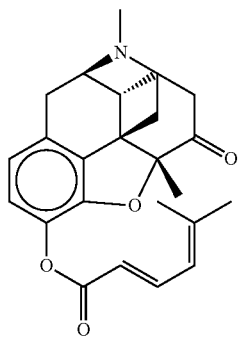
Metopon
5-methylhexadienoate
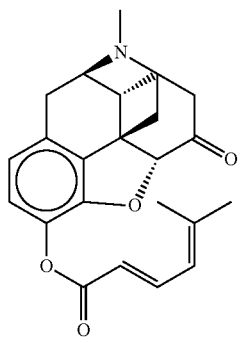
Hydromorphone
5-methylhexadienoate
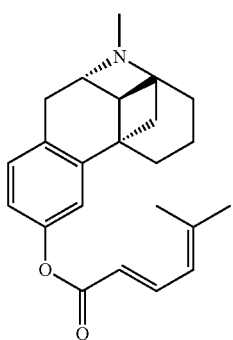
Levorphanol
5-methylhexadienoate
TABLE 7-continued
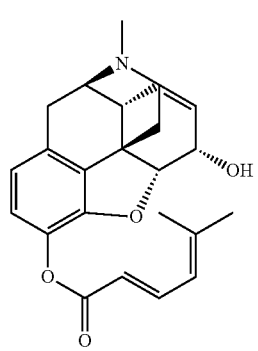
Morphino-3-
(5-methyl)hexadienoate
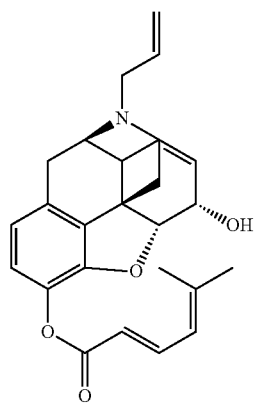
Nalorphino-3-
(5-methyl)hexadienoate
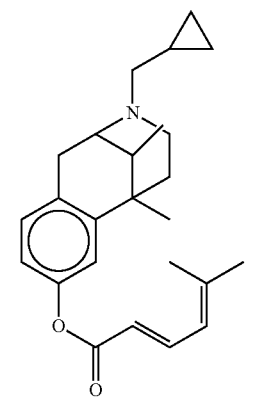
Cyclazocine
5-methylhexadienoate
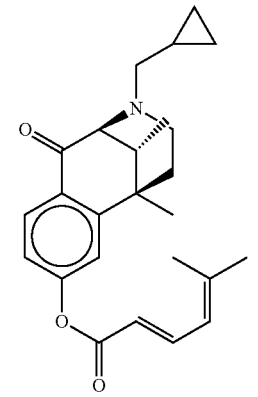
Ketocyclazocine
5-methylhexadienoate TABLE 7-continued

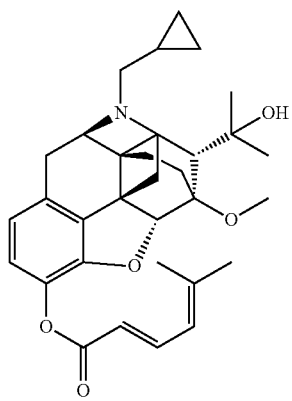

Diprenorphine
5-methylhexadienoate

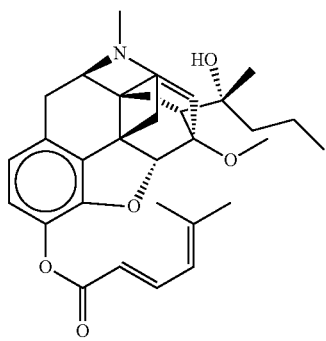

Etorphine
5-methylhexadienoate

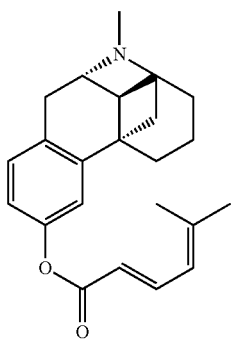

Levorphanol
5-methylhexadienoate

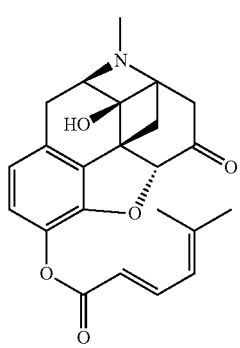

Oxymorphone
5-methylhexadienoate

TABLE 7-continued

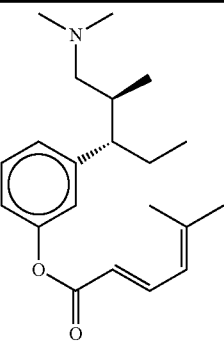

Tapentadol
5-methylhexadienoate

Example 8—Molecular Docking of Nalbuphine/Naloxone Opioid Antagonists Into μ-Opioid Receptor The human μ-opioid receptor crystal structures were downloaded from the RCSB Protein Data Bank [PDB entry: 4DKL, https://www.rcsb.org/structure/4DKL). The in silico screening was carried out with the MOE Dock program, part of the MOE Simulation module 2014.0901. The dissociation constants (Ki) were calculated from the equation $\Delta G = RT \ln(K_i)$, where $\Delta G$ represents binding free energy which is equivalent to GBVI/WSA dG scoring function, R is the gas constant and T the temperature. The Ki was computed starting from the binding free energy values at a fixed temperature (300 K).

Both antagonists nalbuphine and naloxone demonstrate the key interaction of Asp 147 with their ammonium group. It is known that this bonding to Asp 147 is typical for the most known opioid agonists/antagonists. The other duplicate interaction of nalbuphine and naloxone is bonding of the hydroxyl group attached to the aryl ring (3-position) to the water molecule, which contributes in stabilizing the inactive state of opioid receptors. Differently from nalbuphine, the hydroxyl group of naloxone attached to the tertiary carbon atom (14-position) participates in additional hydrogen bonding to Asp 147.

Figure 9A:
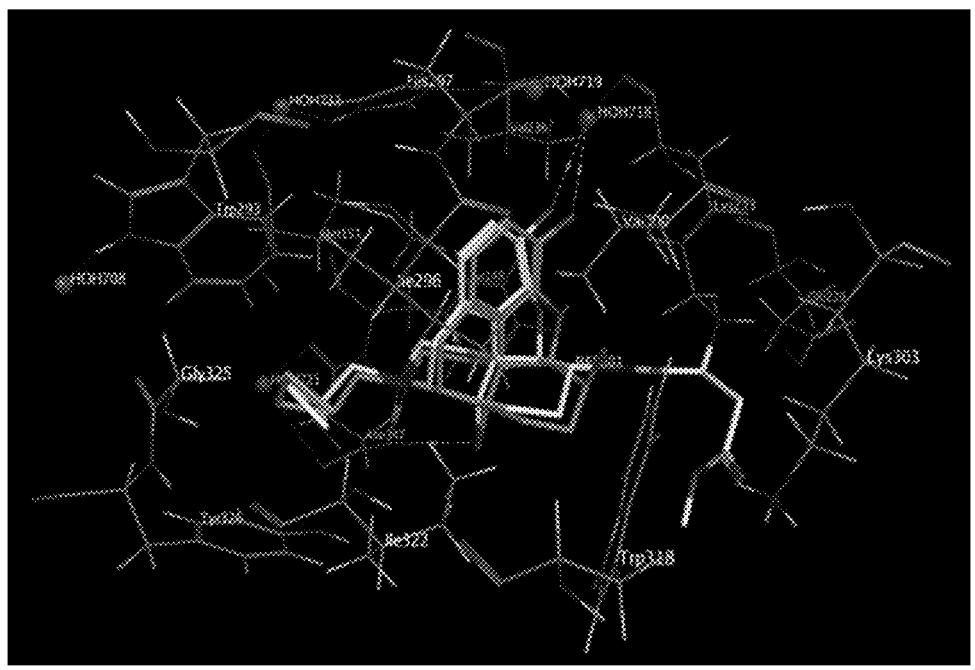
FIG. 9A illustrates the binding mode and molecular interactions of the most energetically favored conformer of nalbuphine superposed with co-crystallized ligand β-FNA.
Figure 9B:
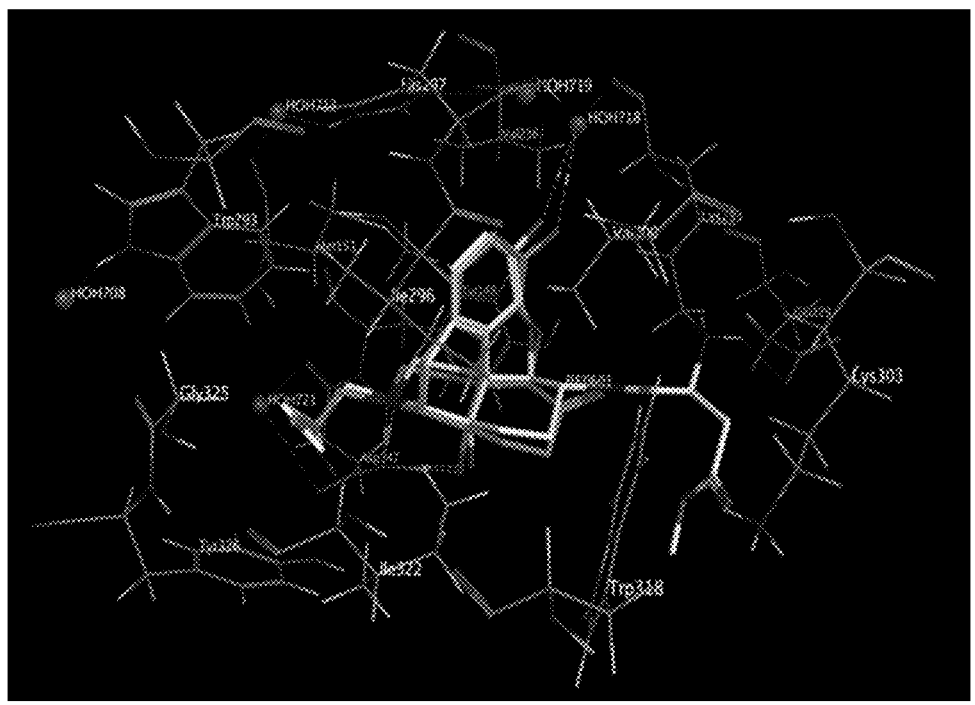
FIG. 9B illustrates the binding mode and molecular interactions of the most energetically favored conformer of naloxone superposed with co-crystallized ligand β-FNA.

FIG. 9A illustrates the binding mode and molecular interactions of the most energetically favored conformer of nalbuphine superposed with co-crystallized ligand β-FNA. FIG. 9B illustrates the binding mode and molecular interactions of the most energetically favored conformer of naloxone superposed with co-crystallized ligand β-FNA.

Nalbuphine and naloxone is bonding of the hydroxyl group attached to the aryl ring (3-position) to the water molecule, which contributes in stabilizing the inactive state of opioid receptors. Differently from nalbuphine, the hydroxyl group of naloxone attached to the tertiary carbon atom (14-position) participates in additional hydrogen bonding to Asp 147.

Figure 10A:
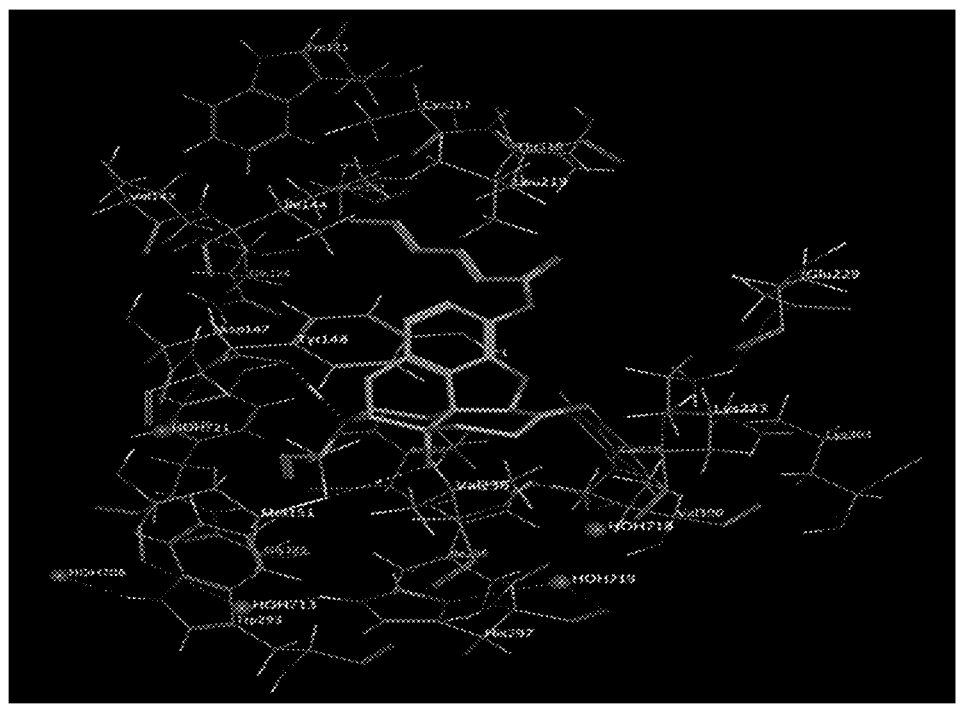
FIG. 10A illustrates the binding mode and molecular interactions of the most energetically favored conformer of NX-90 in the binding site of 4DKL.

FIG. 10A illustrates the binding mode and molecular interactions of the most energetically favored conformer of NX-90 in the binding site of 4DKL.

Figure 10B:
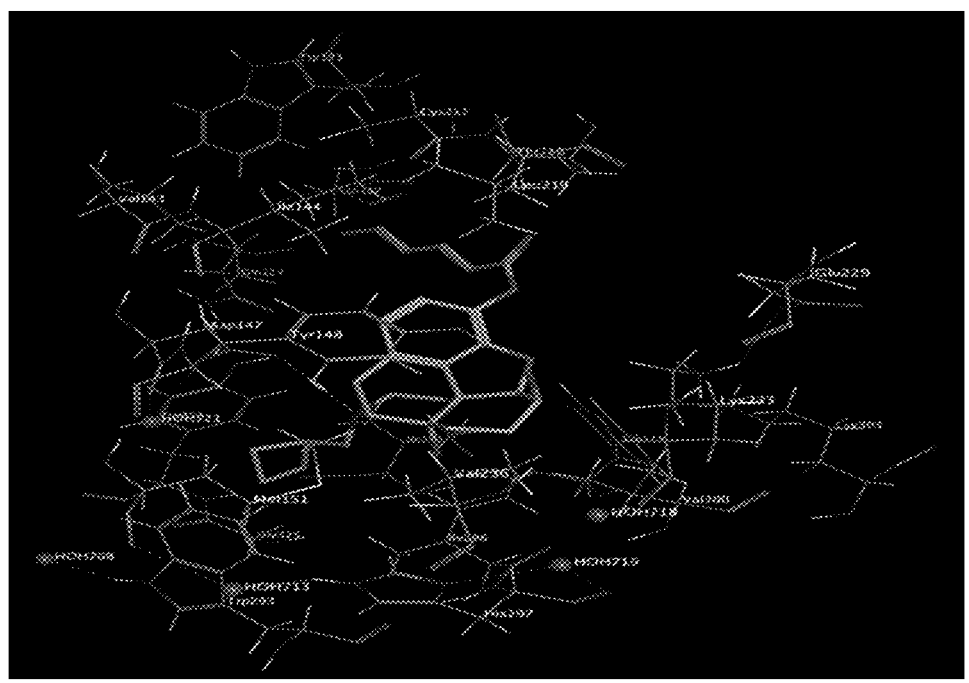
FIG. 10B illustrates the binding mode and molecular interactions of the most energetically favored conformer of NB-33 in the binding site of 4DKL.

FIG. 10B illustrates the binding mode and molecular interactions of the most energetically favored conformer of NB-33 in the binding site of 4DKL.

Figure 10C:
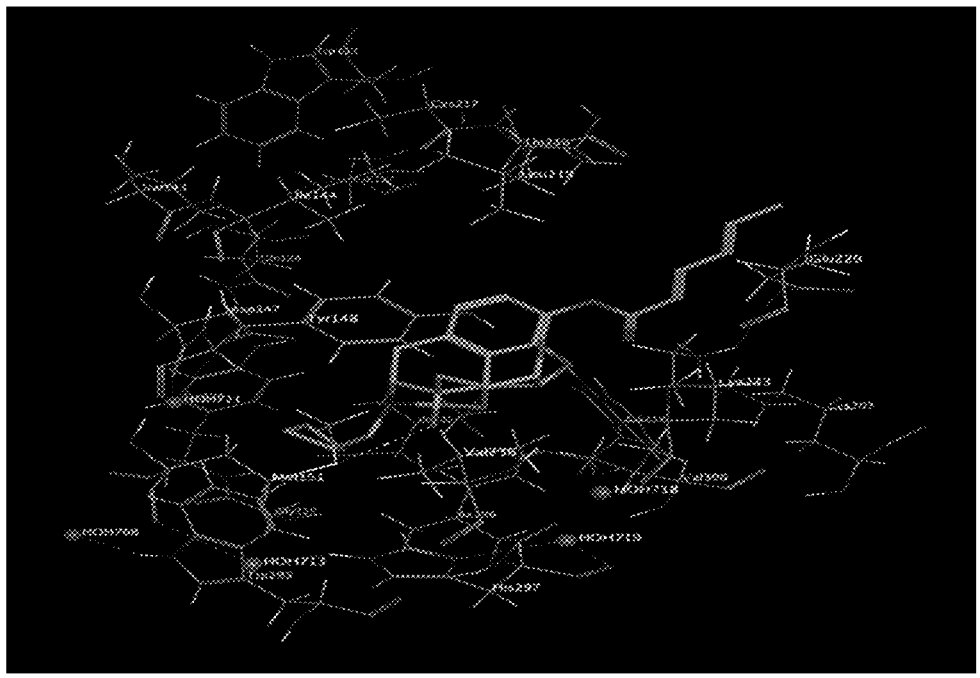
FIG. 10C illustrates molecular interaction with Met 151 shown by the conformer of NB-33 with the binding mode similar to the most energetically favored conformer.

FIG. 10C illustrates molecular interaction with Met 151 shown by the conformer of NB-33 with the binding mode similar to the most energetically favored conformer.

Figure 10D:
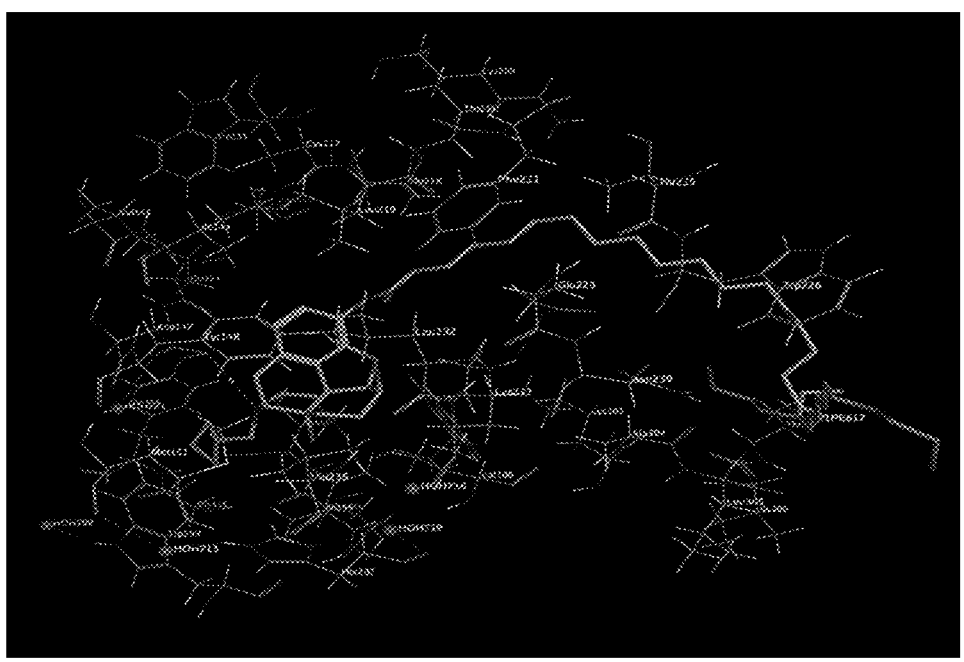
FIG. 10D illustrates the binding mode and molecular interactions of the most energetically favored conformer of NB-39 in the binding site of 4DKL.

FIG. 10D illustrates the binding mode and molecular interactions of the most energetically favored conformer of NB-39 in the binding site of 4DKL.

Figure 11A:
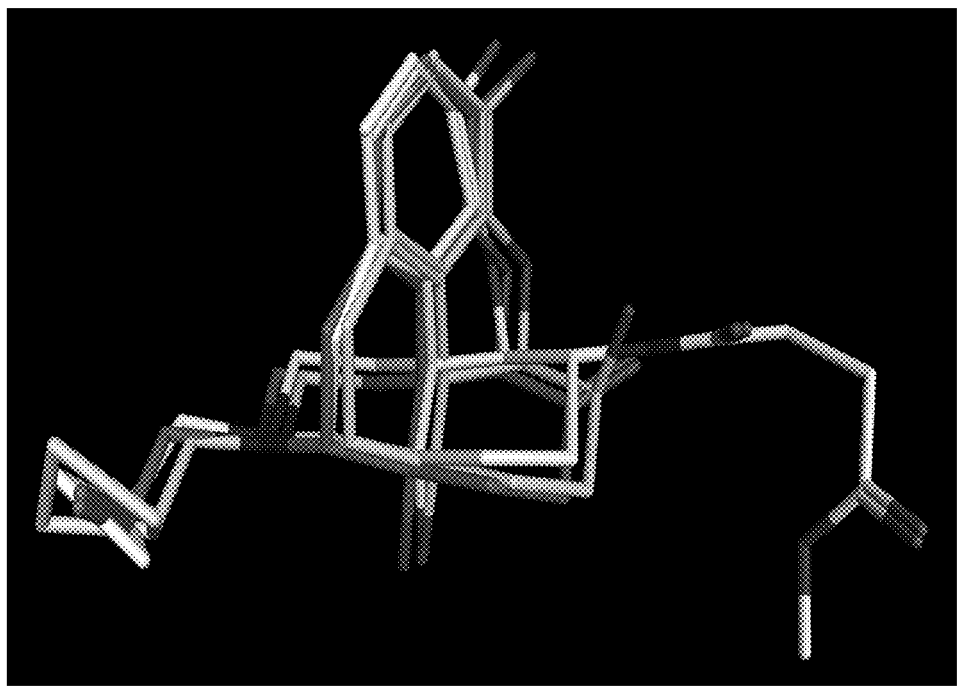
FIG. 11A illustrates the most energetically favored conformer of nalbuphine (yellow), naloxone (pink) and co-crystalized β-FNA (white) superposed in the opioid binding site of 4DKL.
Figure 11B:
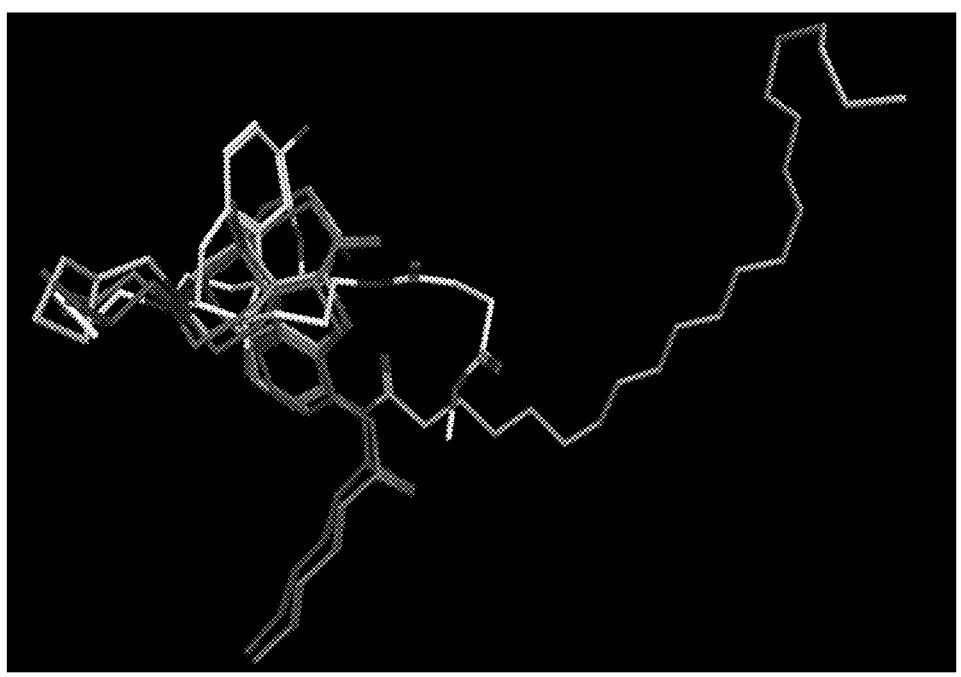
FIG. 11B illustrates the most energetically favored conformers of NX-90 (blue), NB-33 (red), NB-39 (cyan) and co-crystalized β-FNA (white) superposed in the opioid binding site of 4DK.

FIG. 11A illustrates the most energetically favored conformer of nalbuphine (yellow), naloxone (pink) and co-crystalized β-FNA (white) superposed in the opioid binding site of 4DKL. FIG. 11B illustrates the most energetically favored conformers of NX-90 (blue), NB-33 (red), NB-39 (cyan) and co-crystalized β-FNA (white) superposed in the opioid binding site of 4DK.

Computed dissociation constants (Ki) of NX-90, NB-33, NB-39 established the higher affinity to the μ-receptor (NB-33, NB-39) or a little lower affinity (NX-90) in comparison to the affinities of nalbuphine and naloxone. Analogously to the most energetically favored conformers of naloxone and nalbuphine, NX-90, NB-33 and NB-39 retain the crucial hydrogen bonding to the residue of Asp147. In this docking mode the "message" attached to the nitrogen atom is delivered to the correct "address" sited on the exact area of the binding pocket of the μ-receptor. However, unlike the binding mode of known μ-antagonists (e.g. nalbuphine and naloxone; FIG. 11A) the rigid frames of NX-90, NB-33 and NB-39 are rotated by 180° in the binding site (FIG. 11B). Conversely, the binding mode that describes binding of nalbuphine and naloxone is not possible for all computed conformers of NB-33, NB-39 and NX-90.

Furthermore, both NX-90 and NB-33 have the unique hydrogen bonding to Met 151 through the hydroxyl group attached to the tertiary carbon atom (14-position). This interaction makes both NX-90 and NB-33 different from NB-39 which hydroxyl group at cyclohexane fragment (6-position) forms the hydrogen bond with Lys A233 instead. The second differentiating factor for both NX-90 and NB-33 is that the rigid conjugated system of the residue of hexadienoic acid has the extraordinary hydrophobic cylindrical molecular surface. Simultaneously, the residues Cys217, Thr218, Asn127, Gln124, Trp133, Leu219 build the extra complementary hydrophobic molecular surface surrounding this hexadienyl "tail" inside the binding pocket (FIGS. 12A and 12B), whereas no discernible hydrophobic surface exists in the areas of binding site surrounding the highly flexible and lacking conjugation docosanoyl "tail" (FIG. 12C).

Figure 12A:
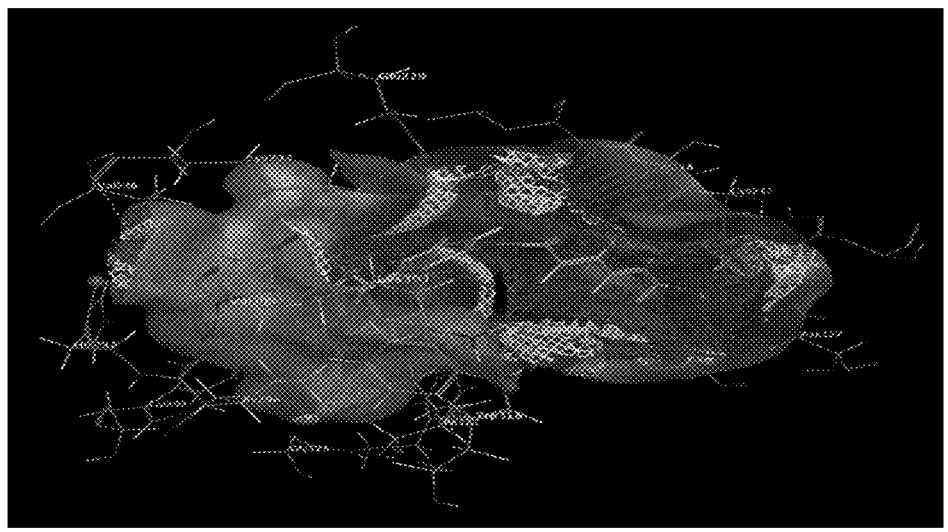
FIGS. 12A-C show Hydrophobic (red) and hydrophilic (yellow) contact preference areas on the molecular surface of the binding site of 4DKL with the docked conformer of NX-90, NB-33 and NB-39, respectively, in accordance with at least one embodiment.
Figure 12B:
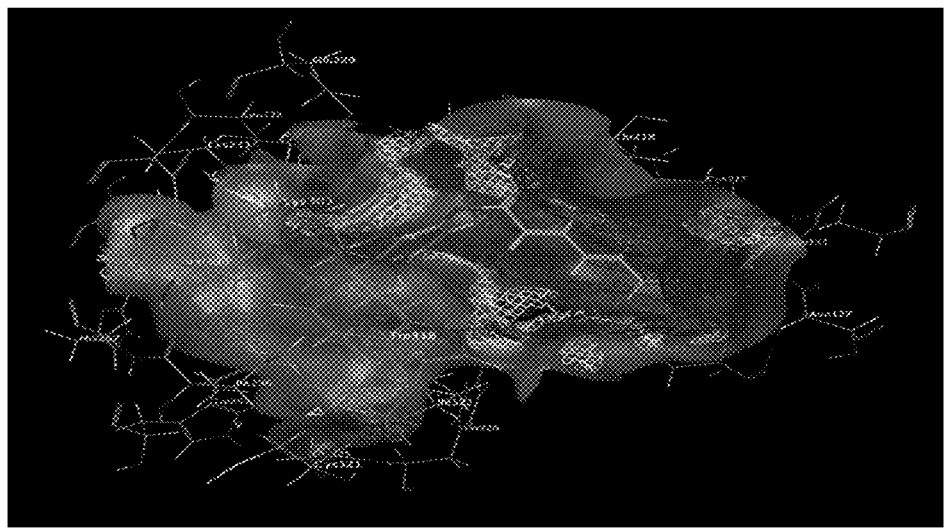
Figure 12C:
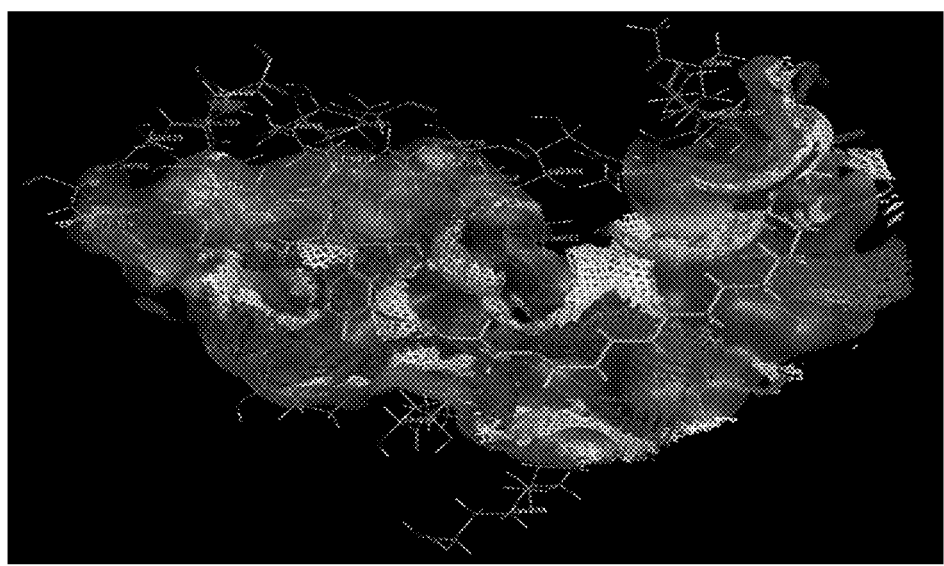

FIGS. 12A-C show Hydrophobic (red) and hydrophilic (yellow) contact preference areas on the molecular surface of the binding site of 4DKL with the docked conformer of NX-90, shown in FIG. 12A; NB-33, shown in FIG. 12B and NB-39, shown in FIG. 12C.

These examples, particularly in FIGS. 9-12 confirm at least one feature of the present invention, i.e., that modifying an opioid with a lipophilic moiety with at least two conjugated double bonds improves interactions with the opioid receptor.

These examples also confirm another feature of the present invention, i.e., that modifying an opioid with a lipophilic moiety with at least two conjugated double bonds improves interactions with the opioid receptor by rotating the opioid in the active site by 180° C. and creating additional modes of interactions with the receptor including a unique hydrophobic pocket.

These examples further confirm another feature of the present invention, i.e., that modifying an opioid with a lipophilic moiety with at least two conjugated double bonds changes properties of the opioid at least in some embodiments of the present invention.

These examples confirm yet another feature of the present invention, i.e., that modifying an opioid with a lipophilic moiety with at least two conjugated double bonds improves antagonistic properties of the opioid at least in some embodiments of the present invention.

Improved Performance of Opioid Receptor Antagonists

As described above, in addition to the improved performance and analgesic qualities of opiates, the present invention also includes at least one embodiment where hexadienoate improves performance of opioid receptor antagonists, such as, for example, Naloxone.

In at least one embodiment, the present invention, and particularly the hexadienoate has been combined and tested with at least one specie (or multiple species) from the Naloxone group or compound.

In at least one embodiment of the present invention, the Naloxone, having hexadienoate, is included in the molecule, and provides substantially more effective and long-lasting neutralizing/sobering effect when administered to a subject.

In at least one embodiment of the present invention, a compound NX-90 and NX-97 having the below formula has been synthesized and analyzed, as shown in TABLE 8 below.

TABLE 8

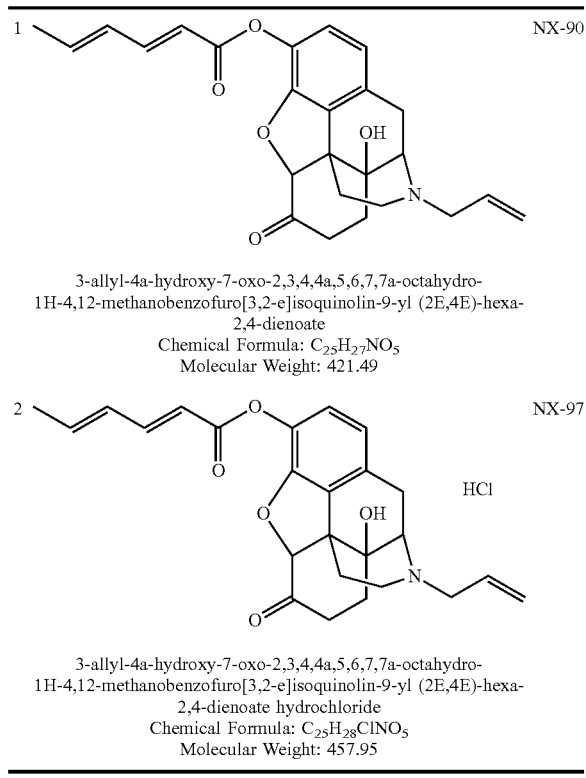

1. NX-90
3-allyl-4a-hydroxy-7-oxo-2,3,4,4a,5,6,7,7a-octahydro-1H-4,12-methanobenzofuro[3,2-e]isoquinolin-9-yl (2E,4E)-hexa-2,4-dienoate
Chemical Formula: $C_{25}H_{27}NO_5$
Molecular Weight: 421.49

2. NX-97
3-allyl-4a-hydroxy-7-oxo-2,3,4,4a,5,6,7,7a-octahydro-1H-4,12-methanobenzofuro[3,2-e]isoquinolin-9-yl (2E,4E)-hexa-2,4-dienoate hydrochloride
Chemical Formula: $C_{25}H_{28}ClNO_5$
Molecular Weight: 457.95

Sobering effect may be noted when administered to a subject. This compound may be utilized and synthesized in accordance with at least one embodiment of the present invention is referenced and named Naloxone-sorbate, (NX-90). The preparation of the compound based on at least one embodiment may proceed as follows.

EDCI.HCl (1.36 g, 7.12 mmol) was added to hexadienoic acid (0.74 g, 6.61 mmol) in THF (50 mL) at 0° C. with stirring. Triethylamine (1.39 g, 13.8 mmol) was added. Stirring for 2 h at 0° C. Naloxone hydrochloride (2.00 g, 5.5 mmol and 4-dimethylaminopyidine (0.10 g, 0.82 mmol) were added at 0° C. The stirring was continued for 1 h at 0° C. and at room temperature overnight. The reaction mixture was filtered, filtrate was evaporated, and the residue was twice purified by column chromatography (silicagel, EtOAc/Heptanes/Triethylamine, 2:1:0.5%). The white crystals were formed after evaporation of selected fractions, yield 0.75 g (32%), purity 98% by HPLC. The structure was confirmed by NMR $^1$H.

The properties of the NX-90 compound have been studied and the following results and specific benefits, including stability data, have been obtained and confirmed.

TABLE 9

NX-90 Stability (GIF) Batch Number Alpha-1-91 (Tested by Alfacheminvent LLC).

PRODUCT NAME: NX-90

| BATCH NO.: | MFG DATE: | SAMPLE SIZE: | PACKAGING |
|---|---|---|---|
| Alpha-1-91 | Mar. 21, 2019 | 5.0 MG/2.0 ML | TYPE: |
|  |  |  | Glass vial (upright) |
| ASSAY | STABILITY TESTING |  | STATUS: |
| CONDITIONS: | INTERVALS: |  | COMPLETED: |
| GIF, 37° C., shaker | INITIAL, 1, 2, 4, 8, 24 HRS |  | Mar. 22, 2019 |

| TEST | Specifications | Initial | 1 h | 2 h | 4 h | 8 h | 24 h |
|---|---|---|---|---|---|---|---|
| Product Appearance | Clear solution | Conforms | Conf. | Conf. | Conf. | Conf. | Conf. |
| HPLC Assay: (Area %) | Report results | 99.3 | 99.2 | 99.3 | 98.4 | 95.1 | 93.0 |
| Single impurity: RRT = 0.93 (Area %) | Report results | 0.6 | 0.7 | 0.6 | 0.6 | 0.7 | 0.6 |
| Single impurity: RRT = 0.67 (Area %) | Report results | — | — | — | 0.9 | 2.3 | 5.5 |

Based on the results and observations, shown in Table 9, the NX-90 has shown significant improvements over the well-known drug Naloxone.

Examples of the combination of NB-33 or similar compounds with different opiates and NX-90 with opiate antagonists in accordance with at least one embodiment of the present invention is further shown in Appendix A.

It is well documented and commonly known that opioids can be used for the treatment of the following medical conditions: pain management, a palliative care, a postoperative anesthesiology, a skin disorder, an addiction, a locomotive disorder, a levodopa-induced dyskinesias (LID) in Parkinson's disease, a dyskinesias associated with Tourette's syndrome, a tardive dyskinesia and a Huntington's disease and others. The potency and effectiveness of the opioids used for the treatment of these medical conditions affects how successful the treatment is.

Respectively, the higher engagement of opioid receptors produces more effective results for the treating such conditions in accordance with at least one embodiment of the present invention. For example, opioids modified with Hexadienoates will be more effective in treating the aforementioned conditions, because they have higher engagement of opioid receptors.

Thus, in at least one embodiment of the present invention, one of the composition compounds that is formulated based on the present invention, as for example NB-33 or NX-90 (or others) may be utilized for treatment of one of the medical conditions such as a pain management, a palliative care, a postoperative anesthesiology, a skin disorder (e.g. pruritus), an addiction (detox or management), and/or a locomotive disorder (e.g. levodopa-induced dyskinesias (LID) in Parkinson's disease, and the dyskinesias associated with Tourette's syndrome, tardive dyskinesia and Huntington's disease).

Example 9

TABLE 10 demonstrates human recombinant opiate receptor data for NX 90.

TABLE 10 demonstrates human recombinant opiate receptor data for NX 90.

| Assay | NX-90 <1 uM | NX-90 >1 uM |
|---|---|---|
| mu (MOR) (h) (agonist effect) |  |  |
| mu (MOR) (h) (antagonist effect) | X | X |
| kappa (KOR) (h) (agonist effect) |  |  |
| kappa (KOR) (h) (antagonist effect) | X | X |
| delta (DOR) (h) (agonist effect) |  |  |
| delta (DOR) (h) (antagonist effect) |  | X |

Human recombinant opiate receptor (mu, kappa or delta) expressed in CHO-K1 cells were used. Test compound (NX-90)/or vehicle was incubated with the cells (4×10E5/mL) in modified HBSS pH 7.4 buffer at 370 C for 30 min. The reaction was evaluated for cAMP levels (cAMP and/or calcium flux) by TR-FRET. Compounds were screened at 0.1, 0.3 and 1 uM by Eurofins Pharma Discovery Services.

Data for compound NX-90 is summarized in Table 10. It shows that NX-90 is not a pharmacologically inert compound and has a distinct opioid signature of its own, similar to the pharmacological profile of naloxone. Separately, it shown that NB-33 is not a pharmacologically inert compound and has a distinct opioid signature of its own, similar to the pharmacological profile of NB.

These results are highly surprising as the prior art suggests that such modifications of 3-phenoxy position with fatty acids (e.g. NB-39) are pro-drugs and by definition are pharmacologically inert compounds. In accordance with at least one embodiment of the present invention, the NX-90 and NB-33 are shown not pharmacologically inert and are not pro-drugs.

In all cases it is understood that the above-described examples and compounds are merely illustrative of the many possible specific embodiments which represent applications of the present invention. Numerous and varied other arrangements can be readily devised in accordance with the principles of the present invention without departing from the spirit and the scope of the invention.

The invention claimed is:

1. The compound having the chemical formula 3-allyl-4a-hydroxy-7-oxo-2,3,4,4a,5,6,7,7a-octahydro-1H-4,12-methanobenzofuro[3,2-e]isoquinolin-9-yl (2E,4E)-hexa-2,4-dienoate or any pharmaceutically acceptable salts thereof.

2. A composition comprising a pharmaceutically effective amount of the compound of claim 1 and a pharmaceutically acceptable carrier.

3. The compound having the chemical formula 3-(cyclobutylmethyl)-4a,7-dihydroxy-2,3,4,4a,5,6,7,7a-octahydro-1H-4,12-methanobenzofuro[3,2-e]isoquinolin-9-yl (2E,4E)-hexa-2,4-dienoate or any pharmaceutically acceptable salts thereof.

4. A composition comprising a pharmaceutically effective amount of the compound of claim 3 and a pharmaceutically acceptable carrier.

\* \* \* \* \*